(12) United States Patent
Wonneberger et al.

(10) Patent No.: US 9,385,326 B2
(45) Date of Patent: Jul. 5, 2016

(54) TRIANGULENE OLIGOMERS AND POLYMERS AND THEIR USE AS HOLE CONDUCTING MATERIAL

(71) Applicants: BASF SE, Ludwigshafen (DE); MAX-PLANCK-GESELLSCHAFT ZUR FOERDERUNG DER WISSENSCHAFTEN E.V., Munich (DE)

(72) Inventors: Henrike Wonneberger, Mannheim (DE); Ingmar Bruder, Mutterstadt (DE); Robert Send, Karlsruhe (DE); Florian Schluetter, Mainz (DE); Klaus Muellen, Cologne (DE); Milan Kivala, Erlangen (DE)

(73) Assignees: BASF SE, Ludwigshafen (DE); Max-Planck-Gesellschaft zur Foerderung der Wissenschafen e.V., Munich (DE)

( * ) Notice: Subject to any disclaimer, the term of this patent is extended or adjusted under 35 U.S.C. 154(b) by 0 days.

(21) Appl. No.: 14/758,349

(22) PCT Filed: Jan. 14, 2014

(86) PCT No.: PCT/EP2014/050556
§ 371 (c)(1),
(2) Date: Jun. 29, 2015

(87) PCT Pub. No.: WO2014/111365
PCT Pub. Date: Jul. 24, 2014

(65) Prior Publication Data
US 2015/0333275 A1    Nov. 19, 2015

Related U.S. Application Data

(60) Provisional application No. 61/752,509, filed on Jan. 15, 2013.

(51) Int. Cl.
| | |
|---|---|
| *C07D 471/18* | (2006.01) |
| *H01L 51/50* | (2006.01) |
| *H01L 51/00* | (2006.01) |
| *C07D 455/03* | (2006.01) |
| *H01L 51/42* | (2006.01) |
| *H01G 9/20* | (2006.01) |
| *H01L 51/44* | (2006.01) |
| *H01L 27/28* | (2006.01) |
| *H01L 51/05* | (2006.01) |

(52) U.S. Cl.
CPC .......... *H01L 51/0072* (2013.01); *C07D 455/03* (2013.01); *H01G 9/2022* (2013.01); *H01G 9/2027* (2013.01); *H01G 9/2059* (2013.01); *H01L 27/283* (2013.01); *H01L 51/006* (2013.01); *H01L 51/0035* (2013.01); *H01L 51/0059* (2013.01); *H01L 51/4273* (2013.01); *H01L 51/442* (2013.01); *H01L 51/0558* (2013.01); *H01L 51/5012* (2013.01); *H01L 2251/306* (2013.01); *Y02E 10/542* (2013.01); *Y02E 10/549* (2013.01)

(58) Field of Classification Search
USPC .............................. 546/38; 313/504; 136/252
See application file for complete search history.

(56) References Cited

U.S. PATENT DOCUMENTS

| | | |
|---|---|---|
| 2,761,791 A | 9/1956 | Russell |
| 4,927,721 A | 5/1990 | Gratzel et al. |
| 5,350,644 A | 9/1994 | Graetzel et al. |
| 5,463,057 A | 10/1995 | Graetzel et al. |
| 5,525,440 A | 6/1996 | Kay et al. |
| 6,245,988 B1 | 6/2001 | Gratzel et al. |
| 6,335,480 B1 | 1/2002 | Bach et al. |

(Continued)

FOREIGN PATENT DOCUMENTS

| | | |
|---|---|---|
| DE | 10 2005 053 998 A1 | 5/2007 |
| EP | 0 892 411 A2 | 1/1999 |

(Continued)

OTHER PUBLICATIONS

International Search Report issued Mar. 4, 2014 in PCT/EP2014/050556.

(Continued)

*Primary Examiner* — Charanjit Aulakh
(74) *Attorney, Agent, or Firm* — Oblon, McClelland, Maier & Neustadt, L.L.P.

(57) ABSTRACT

The present invention related to thermally stable p-conducting oligomers and polymers of triangulene of formula (I) and their use in dye sensitized solar cells.

(I)

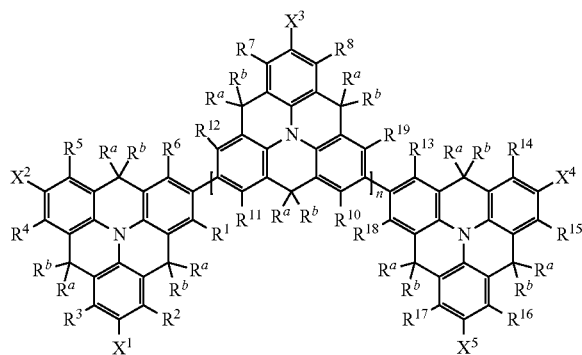

27 Claims, 1 Drawing Sheet

(56) References Cited

U.S. PATENT DOCUMENTS

| | | |
|---|---|---|
| 6,359,211 B1 | 3/2002 | Spitler et al. |
| 8,471,020 B2 | 6/2013 | Reichelt et al. |
| 8,816,081 B2 | 8/2014 | Wonneberger et al. |
| 9,001,029 B2 | 4/2015 | Bruder et al. |
| 9,054,325 B2 | 6/2015 | Benedito et al. |
| 9,087,991 B2 | 7/2015 | Kuhn et al. |
| 9,105,410 B2 | 8/2015 | Wonneberger et al. |
| 2005/0098726 A1 | 5/2005 | Peumans et al. |
| 2005/0224905 A1 | 10/2005 | Forrest et al. |
| 2009/0295275 A1 | 12/2009 | Parham et al. |
| 2013/0334546 A1 | 12/2013 | Wagenblast et al. |
| 2014/0012002 A1 | 1/2014 | Bruder et al. |
| 2014/0066656 A1 | 3/2014 | Bruder et al. |
| 2014/0076397 A1 | 3/2014 | Wagenblast et al. |
| 2014/0103374 A1 | 4/2014 | Koenemann et al. |
| 2014/0301936 A1 | 10/2014 | Schwab et al. |
| 2015/0108415 A1 | 4/2015 | Send et al. |
| 2015/0124268 A1 | 5/2015 | Bruder et al. |
| 2015/0225413 A1 | 8/2015 | Wonneberger et al. |
| 2015/0225418 A1 | 8/2015 | Gessner et al. |

FOREIGN PATENT DOCUMENTS

| | | |
|---|---|---|
| EP | 0 911 841 A2 | 4/1999 |
| EP | 0 991 092 A2 | 4/2000 |
| EP | 1 176 646 A1 | 1/2002 |
| JP | 7-249790 A | 9/1995 |
| JP | 2000-100484 A | 4/2000 |
| JP | 2000-243463 A | 9/2000 |
| JP | 2001-93589 A | 4/2001 |
| JP | 2010-189065 A | 9/2010 |
| WO | WO 98/48433 A1 | 10/1998 |
| WO | WO 98/50393 A1 | 11/1998 |
| WO | WO 00/70655 A2 | 11/2000 |
| WO | WO 02/101838 A1 | 12/2002 |
| WO | WO 2005/019373 A2 | 3/2005 |
| WO | WO 2007/031165 A2 | 3/2007 |
| WO | WO 2007/054470 A1 | 5/2007 |
| WO | WO 2009/013282 A1 | 1/2009 |
| WO | WO 2009/109499 A1 | 9/2009 |
| WO | WO 2012/001628 A1 | 1/2012 |

OTHER PUBLICATIONS

International Preliminary Report on Patentability and Written Opinion issued Jul. 21, 2015 in PCT/EP2014/050556.

Michael Gratzel, et al., "Porphyrin-Sensitized Solar Cells with Cobalt (II/III)—Based Redox Electrolyte Exceed 12 Percent Efficiency" Science, vol. 334, Nov. 4, 2011, 7 Pages.

Hitoshi Sakamoto, et al., "Highly efficient all solid state dye-sensitized solar cells by the specific interaction of CuI with NCS groups II. Enhancement of the photovoltaic characteristics" Organic Electronics, vol. 13, 2012, pp. 514-518.

In Chung, et al., "All-solid-state dye-sensitized solar cells with high efficiency" Nature, vol. 485, May 24, 2012, pp. 486-490.

Jiangbin Xia, et al., "Effect of Doping Anions' Structures on Poly(3,4-ethylenedioxythiophene) as Hole Conductors in Solid-State Dye-Sensitized Solar Cells" Journal of Physical Chemistry, vol. 112, No. 30, 2008, pp. 11569-11574.

K. Peter, et al., "Dual-functional materials for interface modifications in solid-state dye-sensitised $TiO_2$ solar cells" Applied Physics A, vol. 79, 2004, pp. 65-71.

Huaqiang Zhang, et al., "Synthesis, characterization, and electroluminescent properties of star shaped donor-acceptor dendrimers with carbazole dendrons as peripheral branches and heterotriangulene as central core" Tetrahedron, vol. 65, 2009, pp. 4455-4463.

Zhen Fang, et al., "Bridged-triarylamine starburst oligomers as hole transporting materials for electroluminescent devices" Journal of Materials Chemistry, vol. 22, No. 30, XP055102810, Jan. 1, 2012, pp. 15397-15404.

Hui-Seon Kim, et al., "Lead Iodide Perovskite Sensitized All-Solid-State Submicron Thin Film Mesoscopic Solar Cell with Efficiency Exceeding 9%" Scientific Reports, 2012, 7 Pages.

Michael M. Lee, et al., "Efficient Hybrid Solar Cells Based on Meso-Superstructured Organometal Halide Perovskites" Science, vol. 338, Nov. 2, 2012, pp. 643-647.

Jeong-Hyeok Im, et al., "Synthesis, structure, and photovoltaic property of a nanocrystalline 2H perovskite-type novel sensitizer $(CH_3CH_2NH_3)PbI_3$" Nanoscale Research Letters, 2012, 7 Pages.

Kerstin Schmoltner, et al., "A heterotriangulene polymer for air-stable organic field-effect transistors" Polymer Chemistry, vol. 4, No. 20, XP055102949, Apr. 10, 2013, pp. 5337-5344.

Florian Schlutter, et al., "Pi-Conjugated Heterotriangulene Macrocycles by Solution and Surface-supported Synthesis toward Honeycomb Networks" Journal of the American Chemical Society, vol. 135, No. 11, XP055102813, Feb. 25, 2013, pp. 4550-4557.

Saif A. Haque, et al., "Interface Engineering for Solid-State Dye-Sensitized Nanocrystalline Solar Cells: The Use of Ion-Solvating Hole-Transporting Polymers" Advanced Functional Materials, vol. 14, No. 5, XP001195404, May 1, 2004, pp. 435-440.

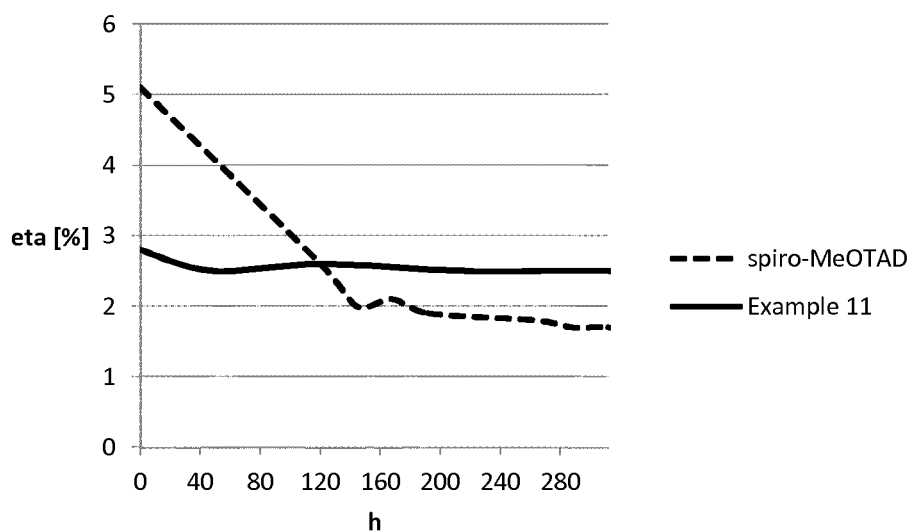

TRIANGULENE OLIGOMERS AND POLYMERS AND THEIR USE AS HOLE CONDUCTING MATERIAL

FIELD OF THE INVENTION

The present invention relates to thermally stable p-conducting oligomers and polymers of triangulene and their use in organic electronics, organic photovoltaics and in particular in dye-sensitized and Perovskite-based solar cells.

Organic electronics and organic photovoltaics are concerned principally with the development of new materials and manufacturing processes for the production of electronic components based on organic semiconductor layers. These include in particular organic field-effect transistors (OFETs), organic electroluminescent devices (hereinafter abbreviated as "EL" devices) and organic solar cells. Great potential for development is ascribed to organic field-effect transistors, for example in storage elements and integrated optoelectronic devices. EL devices in form of organic light-emitting diodes (OLEDs) are especially of interest as an alternative to cathode ray tubes and liquid-crystal displays for producing flat visual display units. A great potential for development is also ascribed to new organic materials which have maximum transport widths and high mobilities for light-induced excited states (high exciton diffusion lengths) and are thus advantageously suitable for use as an active material in so-called excitonic solar cells. With solar cells based on such materials, it is generally possible to achieve very good quantum yields. There is a great need for organic semiconductor compounds with advantageous properties under the respective conditions of use, e.g. a good thermal stability and UV stability, which are suitable for the afore-mentioned applications.

Dye-sensitized solar cells ("DSSCs") are one of the most efficient alternative solar cell technologies at present. In a liquid variant of this technology, efficiencies of over 12% have been reported (e.g. Gratzel et al., Science 2011, 334, 629-634).

The construction of a DSSC is generally based on a transparent substrate (e.g. glass), which is coated with a transparent conductive layer, the working electrode. An n-conductive metal oxide is generally applied to this electrode or in the vicinity thereof, for example a nanoporous titanium dioxide layer ($TiO_2$) of approx. 2-20 µm-thickness. On the surface thereof, in turn, a monolayer of a light-sensitive dye, for example a ruthenium complex or an organic dye, is typically adsorbed, which can be converted to an excited state by light absorption. The counter electrode may optionally have a catalytic layer of a metal, for example platinum, with a thickness of a few µm. The function of the DSSC is based on the fact that light is absorbed by the dye, and electrons are transferred from the excited dye to the n-semiconductive metal oxide semiconductor and migrate thereon to the anode. In liquid DSSC the area between the two electrodes is filled with a redox electrolyte, for example a solution of iodine ($I_2$) and lithium iodide (LiI), which ensures that a photocurrent can be collected at the front and back contacts of the cell.

Cells comprising a liquid electrolyte have specific disadvantages that prevent a wider use of this technology. Thus, in many cases liquid DSSC suffer from durability problems that result from their use of organic liquid electrolytes which cause serious problems, such as electrode corrosion and electrolyte leakage. Therefore, suitable replacements that can be used for hole conduction in lieu of a liquid electrolyte have been searched for. Various materials have therefore been studied for their suitability as solid electrolytes/p-semiconductors.

Various inorganic p-semiconductors such as CuI, $CuBr.3(S(C_4H_9)_2)$ or CuSCN have found use to date in solid-stage DSSCs. With CuI-based, solid DSSCs, for example, efficiencies of more than 7% have been reported by Hitoshi Sakamoto et al. (Organic Electronics 13 (2012), 514-518).

Solid DSSCs comprising fluorine and tin difluoride doped $CsSnI_3$ as hole conducting material and displaying efficiencies of around 10% were reported by In Chung et al. (Nature Vol. 485, May 24, 2012, 486-490). A disadvantage, in particular of the iodide compounds, is the corrositivity.

It is possible to achieve high efficiencies also with low molecular weight organic p-semiconductors. WO 98/48433 A1, for example, reports the use of the organic compound 2,2',7,7'-tetrakis(N,N-di-p-methoxyphenyl-amine)-9,9'-spirobifluorene ("spiro-MeOTAD") in DSSCs as hole transporting material. Nevertheless, the thermal stability of spiro-MeOTAD is still worthy of improvement.

Organic polymers are also used as non-corrosive solid p-semiconductors. Examples thereof include polypyrrole, poly(3,4-ethylenedioxythiophene), carbazole-based polymers, polyaniline, poly(4-undecyl-2,2'-bithiophene), poly(3-octylthiophene), poly(triphenyldiamine) and poly(N-vinylcarbazole). In the case of poly(N-vinylcarbazole), the efficiencies reach up to 2%; with a PEDOT (poly(3,4-ethylenedioxythiophene), polymerized in situ, an efficiency of 2.9% was even achieved (Xia et al. J. Phys. Chem. C 2008, 112, 11569), though the polymers are typically not used in pure form but usually in a mixture with additives. Peter, K. describes in Appl. Phys. A 2004, 79, 65 a concept, wherein a polymeric p-semiconductor is bonded directly to a Ru dye.

WO 2007/031165 A2 describes compounds of the formulae (1) and (2)

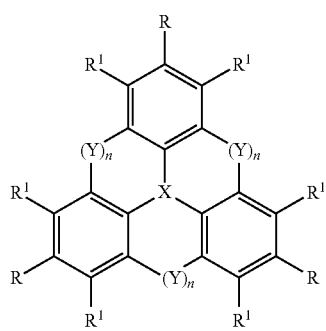

Formula (1)

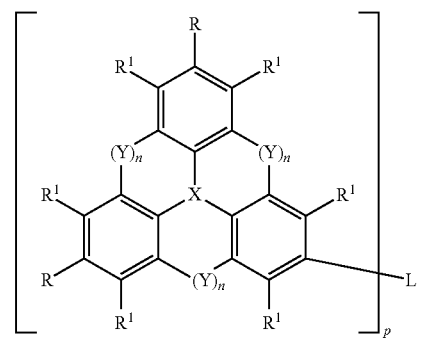

Formula (2)

where p is 2 to 6 depending on the valence of the L group, and the use of those compounds in electroluminescent devices, such as OLED and OFET. The concrete compounds contain only one (hetero)triangulene moiety as central core.

Tetrahedron 65 (2009), 4455-4463 describes the synthesis, characterization and electroluminescent properties of star-shaped donor-acceptor dendrimers with carbazole dendrons as peripheral branches and triangulenes as central core.

J. Mater. Chem., 2012, 22, 15397-15404 describes bridged-triarylamine starburst oligomers as hole transporting materials for electroluminescent devices. This paper discloses inter alia a triangulene tetramer of the following formula:

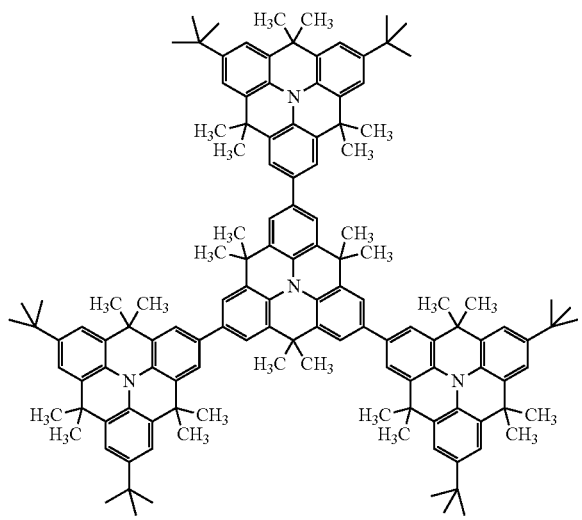 [SMILES: CC(C)(C)c1cc2c3c(c1)C(C)(C)c1cc(C(C)(C)C)cc4c1N3c1c(cc(-c3cc5c6c(c3)C(C)(C)c3cc(-c7cc8c9c(c7)C(C)(C)c7cc(C(C)(C)C)cc%10c7N9c7c(cc(C(C)(C)C)cc7C%10(C)C)C8(C)C)cc7c3N6c3c(cc(-c6cc8c9c(c6)C(C)(C)c6cc(C(C)(C)C)cc%10c6N9c6c(cc(C(C)(C)C)cc6C%10(C)C)C8(C)C)cc3C7(C)C)C5(C)C)cc1C4(C)C)C2(C)C]

In this document, the nonlinear structure of the oligomers is considered of critical importance for the application properties, e.g. a good solubility and high thermal durability. The authors do not present any device data but only DSC (Differential scanning calorimetry) measurements. However, DSC often cannot be correlated with the device performance as the conditions in a device are much more complex (e.g. different materials/interfaces).

A new development in the production of solid DSSC is the use of organometallic Perovskites as light harvesting compounds. H.-S. Kim et al. describe in Scientific Reports, 2: 59, DOI: 10.1038/srep00591 lead iodide Perovskite-sensitized solar cells with an efficiency exceeding 9%. In those cells, Perovskite nanoparticles of methyl ammonium lead iodide are used as absorber material in combination with mesoporous $TiO_2$ as transparent n-type semiconductor and spiro-MeOTAD as p-type hole conductor.

M. M. Lee et al describe in Sciencexpress, 4 Oct. 2012, 10.1126/science.1228604 hybrid solar cells based on meso-superstructured organometal halide Perovskites. In those cells mesoporous alumina is used instead of titanium dioxide. In those cells $Al_2O_3$ does not act as n-type oxide but as a meso-scale "scaffold" upon which the device is structured. Therefore the authors no longer denote the devices as "sensitized" solar cells but as a two-component hybrid solar cells or "meso-superstructured solar cells".

Jeong-Hyeok Im et al. describe in Nanoscale Research letters the synthesis, structure, and photovoltaic property of the nanocrystalline 2H perovskite-type novel sensitizer $(CH_3CH_2NH_3)PbI_3$.

It is an object of the present invention to provide compounds which can be used advantageously as p-semiconductors in diverse fields of application, in particular in solar cells, especially in solar cells on the basis of solid-state hole conductors. With regard to their application properties, these compounds should have a good thermal stability and good hole-conducting properties.

It was now surprisingly found that this object is achieved by linear triangulene oligomers and polymers.

SUMMARY OF THE INVENTION

According to a first aspect of the present invention there is provided a compound of the general formula I

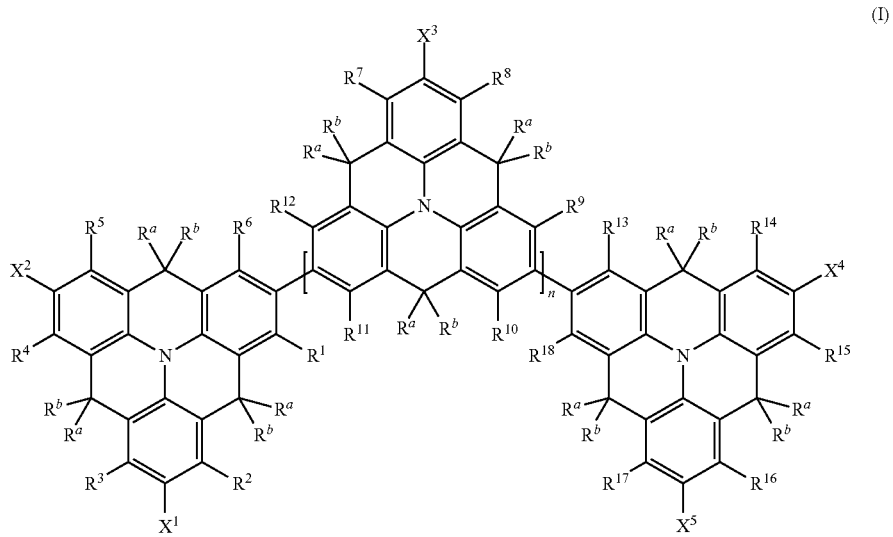

wherein
n is 0 to 100,
$X^1$, $X^2$, $X^3$, $X^4$, and $X^5$ are independently of one another selected from hydrogen, F, Cl, Br, I, CN, $B(OR^c)_2$,
hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, where $E^1$ and $E^2$ are each independently selected from hydrogen, alkyl, cycloalkyl, heterocycloalkyl, aryl or hetaryl, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino, wherein $R^c$ is selected from in each case unsubstituted or substituted alkyl, cycloalkyl or aryl, or wherein two radicals $R^c$ may together form a divalent bridging group selected from in each case unsubstituted or substituted $C_2$-$C_{10}$-alkylene, $C_3$-$C_6$-cycloalkylene and $C_6$-$C_{14}$-arylene, wherein $C_2$-$C_{10}$-alkylene, $C_3$-$C_6$-cycloalkylene and $C_6$-$C_{14}$-arylene may carry one or more identical or different $C_1$-$C_{12}$-alkyl radicals, $R^a$ and $R^b$ are independently of one another selected from hydrogen and unsubstituted $C_1$-$C_6$-alkyl, $R^1$, $R^2$, $R^3$, $R^4$, $R^5$, $R^6$, $R^{13}$, $R^{14}$, $R^{15}$, $R^{16}$, and, if present, $R^7$, $R^8$, $R^9$, $R^{10}$, $R^{11}$ and $R^{12}$ are independently of one another selected from hydrogen, and in each case unsubstituted or substituted alkyl, alkoxy, alkenyl, alkadienyl, alkynyl, cycloalkyl, cycloalkoxy, bicycloalkyl, cycloalkenyl, heterocycloalkyl, heterocycloalkyloxy, aryl, aryloxy, heteroaryl and heteroaryloxy.

A further object of the present invention relates to a composition comprising at least one compound of the general formula (I) as defined above and in the following.

A further object of the present invention relates to a process for the preparation of a compound of the formula (I).

A further object of the present invention relates to a dye-sensitized photoelectric conversion device and to a photoelectric cell, preferably a solar cell, comprising such a device.

A preferred embodiment is a dye-sensitized photoelectric conversion device, comprising:
an electrically conductive layer being part of or forming the working electrode (anode),
a photosensitive layer comprising a semiconductive metal oxide and a chromophoric substance,
a charge transfer layer comprising at least one compound of the formula (I) as defined above and in the following,
an electrically conductive layer being part of or forming the counter electrode (cathode).

A further object of the present invention relates to a Perovskite-based photoelectric conversion device and to a photoelectric cell, preferably a solar cell, comprising such a device.

The photoelectric cell comprises the dye-sensitized photoelectric conversion device and is part of an electric circuit.

A preferred embodiment is a Perovskite-based photoelectric conversion device, comprising:
an electrically conductive layer being part of or forming the working electrode (anode),
a photosensitive layer comprising a Perovskite absorber material,
a charge transfer layer comprising at least one compound of the formula (I) as defined above and in the following,
an electrically conductive layer being part of or forming the counter electrode (cathode).

A further object of the present invention relates to the use of a compound of the formula (I) as defined above and in the following or a composition comprising at least one compound of the formula (I) in dye-sensitized photoelectric conversion devices. It relates in particular to the use of a compound of the formula (I) or a composition comprising at least one compound of the formula (I) as hole-transporting material (p-semiconductor) in dye-sensitized solar cells.

A further object of the present invention relates to the use of a compound of the formula (I) as defined above and in the following or a composition comprising at least one compound of the formula (I) in organic electronics applications or in organic photovoltaics, in particular in organic field-effect transistors and in organic solar cells.

BRIEF DESCRIPTION OF THE DRAWINGS

FIG. 1 Comparison of the efficiency (i) over the lifetime of DSSCs comprising the triangulene nonamer of example 11 as hole transport material (HTM) or comprising spiro-MeOTAD as hole transport material (HTM)

DETAILED DESCRIPTION OF THE INVENTION

Preferably, the compounds of the general formula (I) have a linear structure. In the sense of the invention a linear structure means the no triangulene repeat unit is bound via a direct bond to more than two further triangulene repeat units. In particular, the compounds of the general formula (I) do not have a starburst structure, as described e.g. in J. Mater. Chem., 2012, 22, 15397-15404.

In the context of the invention, the expression "Perovskite-based photoelectric conversion device" denotes devices, wherein the Perovskite component is used in combination with an n-type semiconductive metal oxide (e.g. $TiO_2$) as well as devices, wherein the Perovskite component is used not only as an absorber but also as the n-conductor. In those cells the Perovskite component is used in combination with a carrier material that does not act as an n-type oxide (e.g. $Al_2O_3$).

The expression "halogen" denotes in each case fluorine, bromine, chlorine or iodine, particularly chlorine, bromide or iodine.

As used herein, the expression "unsubstituted or substituted alkyl, alkenyl, alkadienyl, alkynyl, cycloalkyl, bicycloalkyl, cycloalkenyl, heterocycloalkyl, aryl or heteroaryl" refers to unsubstituted or substituted alkyl, unsubstituted or substituted alkenyl, unsubstituted or substituted alkadienyl, unsubstituted or substituted alkynyl, unsubstituted or substituted cycloalkyl, unsubstituted or substituted bicycloalkyl, unsubstituted or substituted cycloalkenyl, unsubstituted or substituted heterocycloalkyl, unsubstituted or substituted aryl or unsubstituted or substituted heteroaryl.

In the context of the invention, the expression "unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino" represents unsubstituted or substituted alkyl, unsubstituted or substituted alkoxy, unsubstituted or substituted alkylthio, unsubstituted or substituted (monoalkyl) amino, unsubstituted or substituted (dialkyl)amino, unsubstituted or substituted cycloalkyl, unsubstituted or substituted cycloalkoxy, unsubstituted or substituted cycloalkylthio, unsubstituted or substituted (monocycloalkyl)amino, unsubstituted or substituted (dicycloalkyl)amino, unsubstituted or substituted heterocycloalkyl, unsubstituted or substituted heterocycloalkoxy, unsubstituted or substituted heterocycloalkylthio, unsubstituted or substituted (monoheterocycloalkyl)amino, unsubstituted or substituted (diheterocycloalkyl)amino, unsubstituted or substituted aryl, unsubstituted or substituted aryloxy, unsubstituted or substituted arylthio, unsubstituted or substituted (monoaryl)amino, unsubstituted or substituted (diaryl)amino, unsubstituted or substituted hetaryl, unsubstituted or substituted hetaryloxy, unsubstituted or substituted hetarylthio, unsubstituted or substituted (monohetaryl)amino and unsubstituted or substituted (dihetaryl)amino.

In the context of the present invention, the expression "alkyl" comprises straight-chain or branched alkyl groups. Alkyl is preferably $C_1$-$C_{30}$-alkyl, more preferably $C_1$-$C_{20}$-alkyl and most preferably $C_1$-$C_{12}$-alkyl. Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethylpentyl, n-octyl, 1-methylheptyl, 2-methylheptyl, 1-ethylhexyl, 2-ethylhexyl, 1-propylpentyl, 2-propylpentyl, n-nonyl, 1-methyloctyl, 2-methyloctyl, 1-ethylheptyl, 2-ethylheptyl, 1-propylhexyl, 2-propylhexyl, 1-butylpentyl, n-decyl, 2-methyldecyl, 1-methylnonyl, 2-methylnonyl, 1-ethyloctyl, 2-ethyloctyl, 1-propylheptyl, 2-propylheptyl, 1-butylhexyl, 2-butylhexyl, n-undecyl, 2-ethylnonyl, 1-propyloctyl, 2-propyloctyl, 1-butylheptyl, 2-butylheptyl, 1-pentylhexyl, n-dodecyl, 2-ethyldecyl, 2-propylnonyl, 1-butyloctyl, 2-butyloctyl, 1-pentylheptyl, 2-pentylheptyl, 2-propyldecyl, n-tridecyl, 1-pentyloctyl, 2-pentyloctyl, 1-hexylheptyl, 2-butylnonyl, n-tetradecyl, 1-hexyloctyl, 2-hexyloctyl, 2-pentylnonyl, 2-hexylnonyl, 2-pentyldecyl, 2-butyldecyl, n-hexadecyl, 1-heptyloctyl, 2-heptylnonyl, 2-hexyldecyl, 2-heptyldecyl, n-octadecyl, 2-octyldecyl, neicosyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-undecyltridecyl, 2-decyltridecyl, 2-nonyltridecyl, 2-octyltridecyl, 2-heptyltridecyl, 2-hexyltridecyl, 2-pentyltridecyl, 2-butyltridecyl, 2-propyltridecyl, 2-ethyltridecyl, 2-methyltridecyl, 2-undecyltetradecyl, 2-decyltetradecyl, 2-nonyltetradecyl, 2-octyltetradecyl, 2-heyltetradecyl, 2-hexyltetradecyl, 2-pentyltetradecyl, 2-butyltetradecyl, 2-propyltetradecyl, 2-ethyltetradecyl, 2-methyltetradecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-docosanyltetracosanyl, 2-hexadecyltetracosanyl, 2-pentadecyltetracosanyl, 2-pentadecyltetracosanyl, 2-tetradecyltetracosanyl, 2-tridecyltetracosanyl, 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, 2-butyltetracosanyl, 2-propyltetracosanyl, 2-ethyltetracosanyl, 2-methyltetracosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl and 2-methyloctacosanyl.

The expression alkyl also comprises alkyl radicals whose carbon chains may be interrupted by one or more nonadjacent groups which are selected from —O—, —S—, —NR″—, —C(=O)—, —S(=O)— and/or —S(=O)$_2$—. R″ is preferably hydrogen, alkyl, cycloalkyl, heterocycloalkyl, aryl or hetaryl.

Substituted alkyl groups may, depending on the length of the alkyl chain, have one or more (e.g. 1, 2, 3, 4, 5 or more than 5) substituents. These are preferably each independently selected from Si(alkyl)(O—Si(alkyl))$_2$, Si(aryl)(O—Si(alkyl))$_2$, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^1$E$^2$ where E$^1$ and E$^2$ are each independently hydrogen, alkyl, cycloalkyl, heterocycloalkyl, aryl or hetaryl. Cycloalkyl, heterocycloalkyl, aryl and hetaryl substituents of the alkyl groups may in turn be unsubstituted or substituted; suitable substituents are the substituents mentioned below for these groups.

Carboxylate and sulfonate respectively represent a derivative of a carboxylic acid function and a sulfonic acid function, especially a metal carboxylate or sulfonate, a carboxylic ester or sulfonic ester function or a carboxamide or sulfonamide function. Such derivatives include, for example, esters with $C_1$-$C_4$-alkanols, such as methanol, ethanol, n-propanol, isopropanol, n-butanol, sec-butanol and tert-butanol.

The above remarks regarding alkyl also apply to the alkyl moiety in alkoxy, alkylthio (=alkylsulfanyl), monoalkylamino and dialkylamino.

Alkylene represents a linear saturated hydrocarbon chain having from 1 to 10 and especially from 1 to 4 carbon atoms, such as ethane-1,2-diyl, propane-1,3-diyl, butane-1,4-diyl, pentane-1,5-diyl or hexane-1,6-diyl.

In the context of the present invention, the term "cycloalkyl" denotes a mono-, bi- or tricyclic hydrocarbon radical having usually from 3 to 20, preferably 3 to 12, more preferably 5 to 12, carbon atoms such as cyclopropyl, cyclobutyl, cyclopentyl, cyclohexyl, cycloheptyl, cyclooctyl, cyclododecyl, cyclopentadecyl, norbornyl, bicyclo[2.2.2]octyl or adamantyl.

Substituted cycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^3$E$^4$ where E$^3$ and E$^4$ are each independently hydrogen, alkyl, cycloalkyl, heterocycloalkyl, aryl or hetaryl. In the case of substitution, the cycloalkyl groups preferably bear one or more, for example one, two, three, four or five, $C_1$-$C_6$-alkyl groups. Examples of substituted cycloalkyl groups are especially 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methylcyclooctyl, 2-, 3-, 4- and 5-ethylcyclooctyl, 2-, 3-, 4- and 5-propylcyclooctyl.

The above remarks regarding cycloalkyl also apply to the cycloalkyl moiety in cycloalkoxy, cycloalkylthio (=cycloalkylsulfanyl), monocycloalkylamino and dicycloalkylamino.

In the context of the present invention, the term "aryl" refers to mono- or polycyclic aromatic hydrocarbon radicals. Aryl usually is an aromatic radical having 6 to 24 carbon atoms, preferably 6 to 20 carbon atoms, especially 6 to 14 carbon atoms as ring members. Aryl is preferably phenyl, naphthyl, indenyl, fluorenyl, anthracenyl, phenanthrenyl, naphthacenyl, chrysenyl, pyrenyl, coronenyl, perylenyl, etc., and more preferably phenyl or naphthyl.

Substituted aryls may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, O—Si(aryl)$_3$, Si(alkyl)(O—Si(alkyl)$_3$)$_2$, Si(aryl)(O—Si(alkyl)$_3$)$_2$, SO$_3$H, sulfonate, sulfamino, sulfamide, amidino, NE$^5$E$^6$ where E$^5$ and E$^6$ are each independently hydrogen, alkyl, cycloalkyl, heterocycloalkyl, aryl or hetaryl. The alkyl, alkoxy, alkylamino, alkylthio, cycloalkyl, heterocycloalkyl, aryl and hetaryl substituents on the aryl may in turn be unsubstituted or substituted. Reference is made to the substituents mentioned above for these groups. The substituents on the aryl are preferably selected from alkyl, alkoxy, haloalkyl, haloalkoxy, aryl, fluorine, chlorine, bromine, cyano and nitro. Substituted aryl is more preferably substituted phenyl which generally bears 1, 2, 3, 4 or 5, preferably 1, 2 or 3, substituents.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-chlorophenyl, (2-chloro-6-methyl)phenyl, (2-chloro-6-ethyl)phenyl, (4-chloro-6-methyl)phenyl, (4-chloro-6-ethyl)phenyl.

The above remarks regarding aryl also apply to the aryl moiety in aryloxy, arylthio (=arylsulfanyl), monoarylamino and diarylamino.

In the context of the present invention, the expression "heterocycloalkyl" comprises nonaromatic, unsaturated or fully saturated, cycloaliphatic groups having generally 5 to 8 ring atoms, preferably 5 or 6 ring atoms. In the heterocycloalkyl groups, compared to the corresponding cycloalkyl groups, 1, 2, 3, 4 or more than 4 of the ring carbon atoms are replaced by heteroatoms or heteroatom-containing groups. The heteroatoms or heteroatom-containing groups are preferably selected from —O—, —S—, —NR$^e$—, —C(=O)—, —S(=O)— and/or —S(=O)$_2$—. R$^e$ is preferably hydrogen, alkyl, cycloalkyl, heterocycloalkyl, aryl or hetaryl. Heterocycloalkyl is unsubstituted or optionally bears one or more, e.g. 1, 2, 3, 4, 5, 6 or 7, identical or different radicals. These are preferably each independently selected from alkyl, alkoxy, alkylamino, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^5$E$^6$ where E$^5$ and E$^6$ are each independently hydrogen, alkyl, cycloalkyl, heterocycloalkyl, aryl or hetaryl. Examples of heterocycloalkyl groups are especially pyrrolidinyl, piperidinyl, 2,2,6,6-tetramethylpiperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^7$E$^8$ where E$^7$ and E$^8$ are each independently hydrogen, alkyl, cycloalkyl, heterocycloalkyl, aryl or hetaryl. In the case of substitution, the heterocycloalkyl groups preferably bear one or more, for example one, two, three, four or five, C$_1$-C$_6$-alkyl groups.

The above remarks regarding heterocycloalkyl also apply to the heterocycloalkyl moiety in heterocycloalkoxy, heterocycloalkylthio (=heterocycloalkylsulfanyl), monoheterocycloalkylamino and diheterocycloalkylamino.

In the context of the present invention, the expression "hetaryl" (heteroaryl) comprises heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2, 4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl groups have 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

Substituted hetaryl groups may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^9E^{10}$ where $E^9$ and $E^{10}$ are each independently hydrogen, alkyl, cycloalkyl, heterocycloalkyl, aryl or hetaryl. Halogen substituents are preferably fluorine, chlorine or bromine. The substituents are preferably selected from $C_1$-$C_6$-alkyl, $C_1$-$C_6$-alkoxy, hydroxyl, carboxyl, halogen and cyano.

The above remarks regarding hetaryl also apply to the hetaryl moiety in hetaryloxy, hetarylthio, monohetarylamino and dihetarylamino.

For the purposes of the present invention, the expression "acyl" refers to alkanoyl or aroyl groups which generally have from 2 to 11, preferably from 2 to 8, carbon atoms, for example the acetyl, propanoyl, butanoyl, pentanoyl, hexanoyl, heptanoyl-, 2-ethylhexanoyl, 2-propylheptanoyl, pivaloyl, benzoyl or naphthoyl group.

The groups $NE^1E^2$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Fused ring systems can comprise alicyclic, aliphatic heterocyclic, aromatic and heteroaromatic rings and combinations thereof, hydroaromatic joined by fusion. Fused ring systems comprise two, three or more (e.g. 4, 5, 6, 7 or 8) rings. Depending on the way in which the rings in fused ring systems are joined, a distinction is made between orthofusion, i.e. each ring shares at least one edge or two atoms with each adjacent ring, and peri-fusion in which a carbon atom belongs to more than two rings. Preferred fused ring systems are ortho-fused ring systems.

Depending on the substitution pattern, the compounds of the formula I may have one or more centers of chirality, in which case they are present as mixtures of enantiomers or diastereomers. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

Specific examples of the radicals mentioned in the following formulae and their substituents are:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl; 2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl; ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert_butylphenoxy)sulfonyl and (4-chlorophenoxy)sulfonyl;

diphenylphosphino, di(o-tolyl)phosphino and diphenylphosphinoxido;

fluorine, chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl)-(1,2,3,4-tetrahydroisoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

Specific examples of radicals containing fluorine are the following:

2,2,2-trifluoroethyl, 2,2,3,3,3-pentafluoropropyl, 2,2-difluoroethyl, 2,2,2-trifluoro-1-phenylethylamin, 1-benzyl-2,2,2-trifluoroethyl, 2-bromo-2,2-difluoroethyl, 2,2,2-trifluoro-1-pyridin-2-ylethyl, 2,2-difluoropropyl, 2,2,2-trifluoro-1-(4-methoxyphenyl)ethylamin, 2,2,2-trifluoro-1-phenylethylamin, 2,2-difluoro-1-phenylethylamin, 1-(4-bromo-phenyl)-2,2,2-trifluoroethyl, 3-bromo-3,3- difluoropropyl, 3,3,3-trifluoropropylamin, 3,3,3-trifluoro-n-propyl, 1H,1H,2H,2H-perfluorodecyl, 3-(perfluorooctyl) propyl, pentafluorophenyl, 2,3,5,6-tetrafluorophenyl, 4-cyano-(2,3,5,6)-tetrafluorophenyl, 4-carboxy-2,3,5,6-tetrafluorophenyl, 2,4-difluorophenyl, 2,4,5-trifluorophenyl, 2,4,6-trifluorophenyl, 2,5-difluorophenyl, 2-fluoro-5-nitrophenyl, 2-fluoro-5-trifluoromethylphenyl, 2-fluoro-5-methylphenyl, 2,6-difluorophenyl, 4-carboxamido-2,3,5,6-tetrafluorophenyl, 2-bromo-4,6-difluorophenyl, 4-bromo-2-fluorophenyl, 2,3-difluorophenyl, 4-chloro-2-fluorophenyl, 2,3,4-trifluorophenyl, 2-fluoro-4-iodphenyl, 4-bromo-2,3,5,6-tetrafluorophenyl, 2,3,6-trifluorophenyl, 2-bromo-3,4,6-trifluorophenyl, 2-bromo-4,5,6-trifluorophenyl, 4-bromo-2,6-difluorophenyl, 2,3,4,5-tetrafluorophenyl, 2,4-difluoro-6-nitrophenyl, 2-fluoro-4-nitrophenyl, 2-chloro-6-fluorophenyl, 2-fluoro-4-methylphenyl, 3-chloro-2,4-difluorophenyl, 2,4-dibromo-6-fluorophenyl, 3,5-dichloro-2,4-difluorophenyl, 4-cyano-1-fluorophenyl, 1-chloro-4-fluorophenyl, 2-fluoro-3-trifluoromethylphenyl, 2-trifluoromethyl-6-fluorophenyl, 2,3,4,6-tetrafluorophenyl, 3-chloro-2-fluorophenyl, 5-chloro-2-fluorophenyl, 2-bromo-4-chloro-6-fluorophenyl, 2,3-dicyano-4,5,6-trifluorophenyl, 2,4,5-trifluoro-3-carboxyphenyl, 2,3,4-trifluoro-6-carboxyphenyl, 2,3,5-trifluorophenyl, 4-trifluoromethyl-2,3,5,6-tetrafluorophenyl, 1-fluoro-5-carboxyphenyl, 2-chloro-4,6-difluorophenyl, 6-bromo-3-chloro-2,4-difluorophenyl, 2,3,4-trifluoro-6-nitrophenyl, 2,5-difluoro-4-cyanophenyl, 2,5-difluoro-4-trifluoromethylphenyl, 2,3-difluoro-6-nitrophenyl, 4-trifluoromethyl-2,3-difluorophenyl, 2-bromo-4,6-difluorophenyl, 4-bromo-2-fluorophenyl, 2-nitrotetrafluorophenyl, 2,2',3,3',4',5,5',6,6'-nonabiphenyl, 2-nitro-3,5,6-trifluorophenyl, 2-bromo-6-fluorophenyl, 4-chloro-2-fluoro-6-iodphenyl, 2-fluoro-6-carboxyphenyl, 2,4-difluoro-3-trifluorophenyl, 2-fluoro-4-trifluorophenyl, 2-fluoro-4-carboxyphenyl, 4-bromo-2,5-difluorophenyl, 2,5-dibromo-3,4,6-trifluorophenyl, 2-fluoro-5-methylsulphonylpenyl, 5-bromo-2-fluorophenyl, 2-fluoro-4-hydroxymethylphenyl, 3-fluoro-4-bromomethylphenyl, 2-nitro-4-trifluoromethylphenyl, 4-trifluoromethylphenyl, 2-bromo-4-trifluoromethylphenyl, 2-bromo-6-chloro-4-(trifluoromethyl)phenyl, 2-chloro-4-trifluoromethylphenyl, 3-nitro-4-(trifluoromethyl)phenyl, 2,6-dichloro-4-(trifluoromethyl)phenyl, 4-trifluorophenyl, 2,6-dibromo-4-(trifluoromethyl)phenyl, 4-trifluoromethyl2,3,5,6-tetrafluorophenyl, 3-fluoro-4-trifluoromethylphenyl, 2,5-difluoro-4-trifluoromethylphenyl, 3,5-difluoro-4-trifluoromethylphenyl, 2,3-difluoro-4-trifluoromethylphenyl, 2,4-bis(trifluoromethyl)phenyl, 3-chloro-4-trifluoromethylphenyl, 2-bromo-4,5-di(trifluoromethyl)phenyl, 5-chloro-2-nitro-4-(trifluoromethyl)phenyl, 2,4,6-tris(trifluoromethyl)phenyl, 3,4-bis(trifluoromethyl)phenyl, 2-fluoro-3-trifluoromethylphenyl, 2-lod-4-trifluoromethylphenyl, 2-nitro-4,5-bis(trifluoromethyl)phenyl, 2-methyl4-(trifluoromethyl)phenyl, 3,5-dichloro-4-(trifluoromethyl)phenyl, 2,3,6-trichloro-4-(trifluoromethyl) phenyl, 4-(trifluoromethyl)benzyl, 2-fluoro-4-(trifluoromethyl)benzyl, 3-fluoro-4-(trifluoromethyl)benzyl, 3-chloro-4-(trifluoromethyl)benzyl, 4-fluorophenethyl, 3-(trifluoromethyl)phenethyl, 2-chloro-6-fluorophenethyl, 2,6-dichlorophenethyl, 3-fluorophenethyl, 2-fluorophenethyl, (2-trifluoromethyl)phenethyl, 4-fluorophenethyl, 3-fluorophenethyl, 4-trifluoromethylphenethyl, 2,3-difluorophenethyl, 3,4-difluorophenethyl, 2,4-difluorophenethyl, 2,5-difluorophenethyl, 3,5-difluorophenethyl, 2,6-difluorophenethyl,4-(4-fluorophenyl)phenethyl, 3,5-di(trifluoromethyl)phenethyl, pentafluorophenethyl, 2,4-di(trifluoromethyl)phenethyl, 2-nitro-4-(trifluoromethyl)phenethyl, (2-fluoro-3-trifluoromethyl)phenethyl, (2-fluoro-5-trifluoromethyl)phenethyl, (3-fluoro-5-trifluoromethyl)phenethyl, (4-fluoro-2-trifluoromethyl)phenethyl, (4-fluoro-3-trifluoromethyl)phenethyl, (2-fluoro-6-trifluoromethyl)phenethyl, (2,3,6-trifluoro)phenethyl, (2,4,5-trifluoro)phenethyl, (2,4,6-trifluoro)phenethyl, (2,3,4-trifluoro)phenethyl, (3,4,5-trifluoro)phenethyl, (2,3,5-trifluoro)phenethyl, (2-chloro-5-fluoro)phenethyl, (3-fluoro-4-trifluoromethyl)phenethyl, (2-chloro-5-trifluoromethyl)phenethyl, (2-fluoro-3-chloro-5-trifluoromethyl)phenethyl, (2-fluoro-3-chloro)phenethyl, (4-fluoro-3-chloro)phenethyl, (2-fluoro-4-chloro)phenethyl, (2,3-difluoro-4-methyl)phenethyl-, 2,6-difluoro-3-chlorophenethyl, (2,6-difluoro-3-methyl)phenethyl, (2-trifluoromethyl-5-chloro)phenethyl, (6-chloro-2-fluoro-5-methyl)phenethyl, (2,4-dichloro-5-fluoro)phenethyl, 5-chloro-2-fluorophenethyl, (2,5-difluoro-6-chloro)phenethyl, (2,3,4,5-tetrafluoro)phenethyl, (2-fluoro-4-trifluoromethyl)phenethyl, 2,3-(difluoro-4-trifluoromethyl)phenethyl, (2,5-di(trifluoromethyl))phenethyl, 2-fluoro-3,5-dibromophenethyl, (3-fluoro-4-nitro)phenethyl, (2-bromo-4-trifluoromethyl)phenethyl, 2-(bromo-5-fluoro)phenethyl, (2,6-difluoro-4-bromo)phenethyl, (2,6-difluoro-4-chloro)phenethyl, (3-chloro-5-fluoro)phenethyl, (2-bromo-5-trifluoromethyl)phenethyl and the like.

In the compounds of the formula (I), n is preferably 0 to 50.

In a first preferred embodiment, the compound of the formula (I) is an oligomer having 2 to 15 triangulene repeat units. More preferably, n is 5, 6, 7, 8 or 9. In particular, the compound of the formula (I) is a nonamer, i.e. a compound of the formula (I), wherein n is 7.

In a second preferred embodiment, the compound of the formula (I) is a polymer, wherein n is in a range of from 16 to 100, preferably in a range of from 20 to 75.

In the compounds of the formula (I), the $R^a$ and $R^b$ radicals may have identical or different definitions. In a preferred embodiment, the $R^a$ and $R^b$ radicals have identical definitions.

In a preferred embodiment, the radicals $R^a$ and $R^b$ are independently of one another selected from hydrogen, methyl or ethyl. In particular, $R^a$ and $R^b$ have the same meaning and are all methyl.

In a preferred embodiment, the radicals $R^1$, $R^2$, $R^3$, $R^4$, $R^5$, $R^6$, $R^{13}$, $R^{14}$, $R^{15}$, $R^{16}$, and, if present, $R^7$, $R^8$, $R^9$, $R^{10}$, $R^{11}$ and $R^{12}$ are all hydrogen.

In the compounds of the formula (I), the $X^3$ radicals may have identical or different definitions.

Preferably, the $X^3$ radicals have identical definitions.

In one preferred embodiment, the $X^3$ radicals are all hydrogen.

In a further preferred embodiment, the $X^3$ radicals are selected from in each case unsubstituted or substituted alkyl, alkoxy, alkylthio, cycloalkyl, aryl, aryloxy and arylthio.

In one preferred embodiment, the radicals $X^1$, $X^2$, $X^4$, and $X^5$ are all hydrogen.

In a further preferred embodiment, one of the radicals $X^1$ and $X^2$ is hydrogen and the other is selected from hydrogen and unsubstituted or substituted alkyl, alkoxy, alkylthio, cycloalkyl, aryl, aryloxy and arylthio.

In a further preferred embodiment, one of the radicals $X^4$ and $X^5$ is hydrogen and the other is selected from hydrogen and unsubstituted or substituted alkyl, alkoxy, alkylthio, cycloalkyl, aryl, aryloxy and arylthio.

An especially preferred embodiment of the compounds of the formula (I) is the nonamer of the formula (I.a)

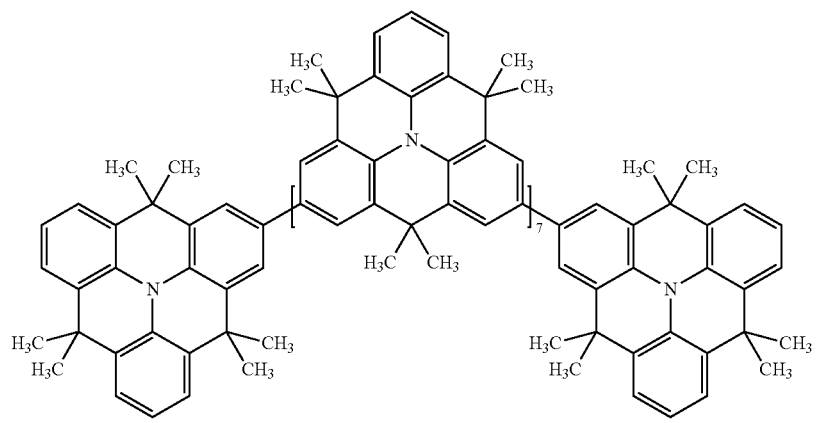

(I.a)

In a second preferred embodiment, the compound of the formula (I) is polymer, having preferably 16 to 100 triangulene repeat units. More preferably, n is in a range of from 20 to 75.

Preferably, the compound of the formula (I) has a number average molecular weight Mn in the range of from 3500 to 30000 g/mol, more preferably 7000 to 25000 g/mol.

Preferably, the compound of the formula (I) has a weight average molecular weight Mn in the range of from 4000 to 60000, more preferably 10000 to 40000 g/mol.

Preferably, the compound of the formula (I) has a polydispersity PD ($=M_w/M_n$) of not more than 6, more preferably not more than 4.

In the sense of this invention $M_n$ and $M_w$ are determined by gel permeation chromatography (GPC). The calibration was effected with a PMMA standard of low dispersity.

An especially preferred embodiment of the compounds of the formula (I) is a polymer of the formula (I.b)

wherein
n is 16 to 100,
$X^2$ and $X^4$ are independently of one another selected from hydrogen, and in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino.

The compounds (I) according to the invention can be prepared by synthetic steps known to the person skilled in the art, such as halogenation, coupling of aryl halides, Suzuki coupling, etc., as depicted in the following schemes.

A central step in the formation of the skeleton of the compounds of the formula (I) is the coupling of aryl halides in the presence of a transition metal catalyst. Therefore, a further object of the invention is a process for the preparation of a compound of the formula I,

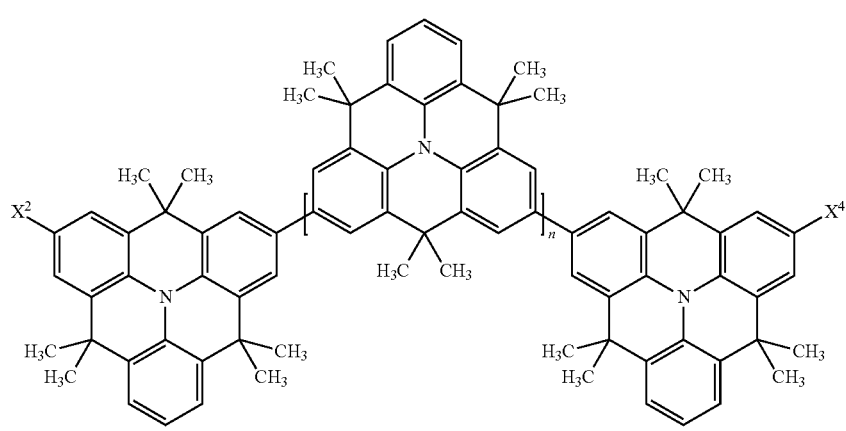

(I.b)

(I)

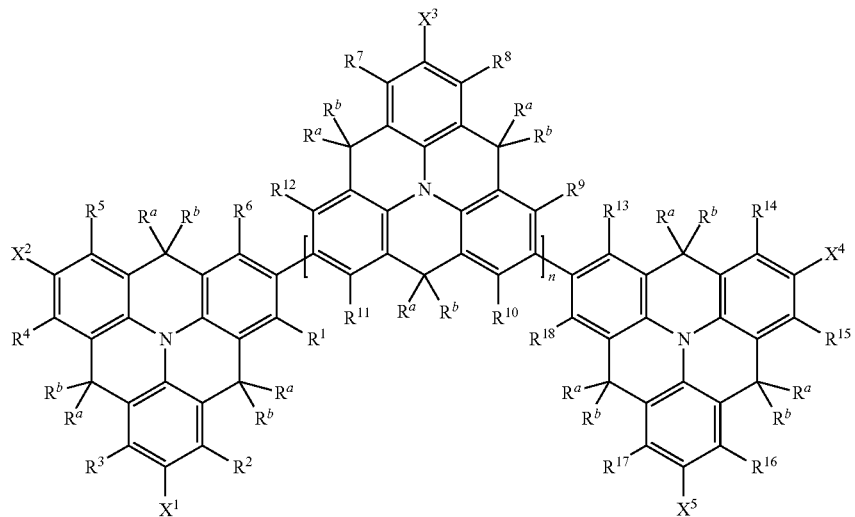

wherein n is 0 to 100, $X^1$, $X^2$, $X^3$, $X^4$, and $X^5$ are independently of one another selected from hydrogen, F, Cl, Br, I, CN, $B(OR^c)_2$, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, where $E^1$ and $E^2$ are each independently selected from hydrogen, alkyl, cycloalkyl, heterocycloalkyl, aryl or hetaryl, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino, wherein $R^c$ is selected from in each case unsubstituted or substituted alkyl, cycloalkyl or aryl, or wherein two radicals $R^c$ may together form a divalent bridging group selected from in each case unsubstituted or substituted $C_2$-$C_{10}$-alkylene, $C_3$-$C_6$-cycloalkylene and $C_6$-$C_{14}$-arylene, wherein $C_2$-$C_{10}$-alkylene, $C_3$-$C_6$-cycloalkylene and $C_6$-$C_{14}$-arylene may carry one or more identical or different $C_1$-$C_{12}$-alkyl radicals, $R^a$ and $R^b$ are independently of one another selected from hydrogen and unsubstituted $C_1$-$C_6$-alkyl, $R^1$, $R^2$, $R^3$, $R^4$, $R^5$, $R^6$, $R^{13}$, $R^{14}$, $R^{15}$, $R^{16}$, and, if present, $R^7$, $R^8$, $R^9$, $R^{10}$, $R^{11}$ and $R^{12}$ are independently of one another selected from hydrogen, and in each case unsubstituted or substituted alkyl, alkoxy, alkenyl, alkadienyl, alkynyl, cycloalkyl, cycloalkoxy, bicycloalkyl, cycloalkenyl, heterocycloalkyl, heterocycloalkyloxy, aryl, aryloxy, heteroaryl and heteroaryloxy, comprising reacting a compound of the formula (A)

(A)

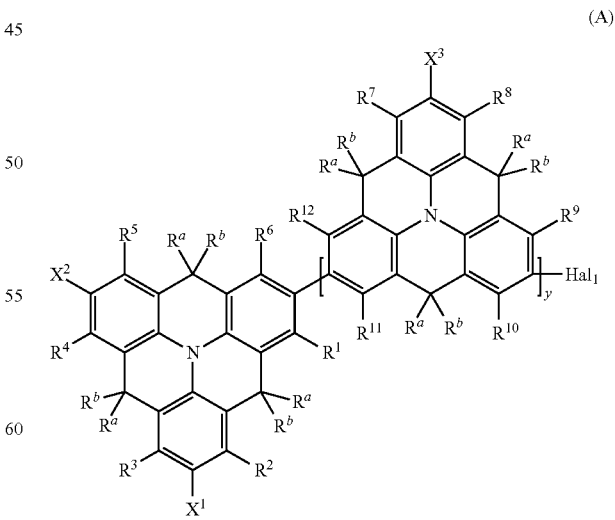

wherein y is 0 to (n-z) and $Hal_1$ is Cl, Br or I with a compound of the formula (B)

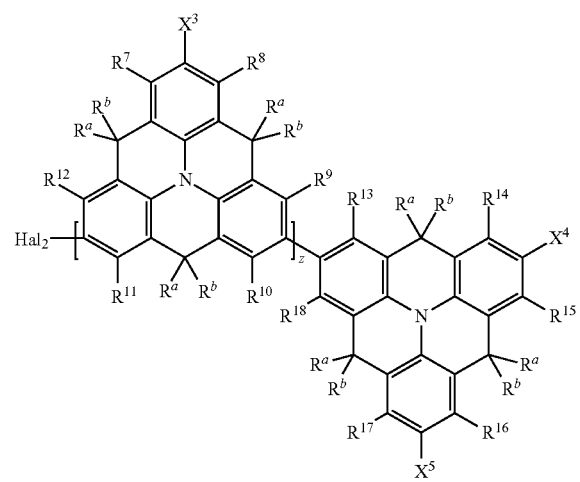

wherein z is 0 to (n-y) and Hal₂ is Cl, Br or I in the presence of a transition metal-containing catalyst, with the proviso that the sum of y+z is n.

Preferably, the employed catalyst comprises Ni as metal, in particular Ni(0). Suitable Ni(0)-mediated aryl-aryl bond formations are described inter alia in Chemical Reviews, 2002, Vol. 102, No. 5, p. 1378-1392. A preferred catalyst is bis(1,5-cyclooctadiene)nickel(0) (=Ni(COD)₂). The catalyst is preferably used in at least equimolar amount per aryl-aryl bond formed. More preferably, the catalyst is used in an 1.1 to 4.0 fold molar excess, in particular an 1.2 to 2.5 fold molar excess, per aryl-aryl bond formed. Preferably, the Ni(0) catalyst further contains bipyridine.

In order to provide suitable starting materials for the preparation of the compounds of the formula (I), a triangulene compound can be subjected to a halogenation, in particular a bromination or iodation. Thus, e.g. the bromination with N-bromosuccinimide (NBS) and the iodation with N-iodosuccinimide (NIS) allow the functionalization of the 2-, 6- and 10-position of the triangulene skeleton with 1, 2 or 3 halogene equivalents, as depicted in scheme 1.

Scheme 1:

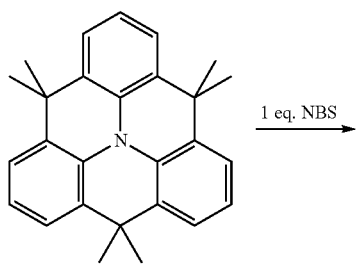

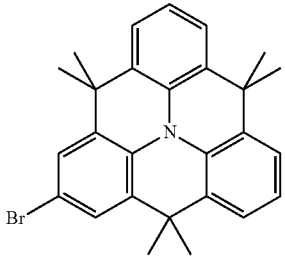

The halogenated compounds can be directly employed in the synthesis of the compounds (I) or subjected to a further functionalization using other reactive groups, for example boron ester groups that are capable of reacting in a Suzuki type coupling reaction. The obtained boron ester compounds in turn can be directly employed in a coupling reaction for the synthesis of the compounds (I) or subjected to a further functionalization. Thus, the compounds (I) bearing at least one boron ester groups can be subjected to a halogenation, in particular a bromination or iodation, as mentioned above. Scheme 2 depicts the bromination of a triangulene, followed by conversion of the bromine group to a boron ester group and a further bromination.

Suitable diboron compounds are compounds of the formula $(R^cO)_2B-B(OR^c)_2$, wherein $R^c$ has the afore-mentioned meaning. Preferably, the diboron compound (B) is selected from compounds of the formula (B1)

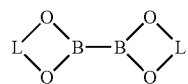

(B1)

wherein L is selected from unsubstituted linear $C_2$-$C_{10}$-alkylene or linear $C_2$-$C_{10}$-alkylene substituted by 1, 2, 3, 4, 5 or 6 $C_1$-$C_{10}$-alkyl groups.

Preferably, in the compounds (B1) L is selected from unsubstituted linear $C_2$-$C_3$-alkylene or linear $C_2$-$C_3$-alkylene substituted by 1, 2, 3 or 4 $C_1$-$C_4$-alkyl groups.

In particular, the diboron compound (B) is selected from bis(pinacolato)diboron, bis(2,2-dimethyl-1,3-propanediolato)diboron (=bis(neopentyl glycolato)diboron), bis(1,1,3,3-tetramethyl-1,3-propanediolato)diboron, bis(4,5-pinandiolato)diboron and bis(1,2-benzenediolato)diborone. Particular preference is given to bis(pinacolato)diboron.

The borylation is preferably performed in the presence of a transition metal-containing catalyst. A suitable transition metal-containing catalyst is [1,1'-bis(diphenylphosphino)ferrocene]dichloropalladium(II) ($Pd(dppf)Cl_2$).

Typically, the transition metal catalyst is used in an amount of from 0.05 to 20% by weight, more preferably from 0.1 to 10% by weight, based on the weight of the compound to be borylated. The borylation is preferably carried out at a temperature in the range from 0 to 200° C., more preferably in the range from 10 to 180° C. and in particular in the range from 20 to 150° C. The reaction is usually performed in an aprotic solvent. Suitable aprotic solvents are ethers, such as dioxane and diglyme (bis(2-methoxyethyl) ether), dimethylformamide, N-methylpyrrolidone, $(CH_3)_2SO$, dimethyl sulfone, sulfolane, cyclic urea such as 1,3-dimethyl-3,4,5,6-tetrahydro-2(1H)-pyrimidinone (DMPU) and imidazolidin-2-one or mixtures thereof. In a preferred embodiment, the reaction is performed under an inert gas atmosphere. Suitable inert gases are for example nitrogen or argon.

Scheme 2:

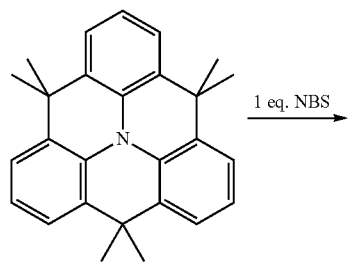

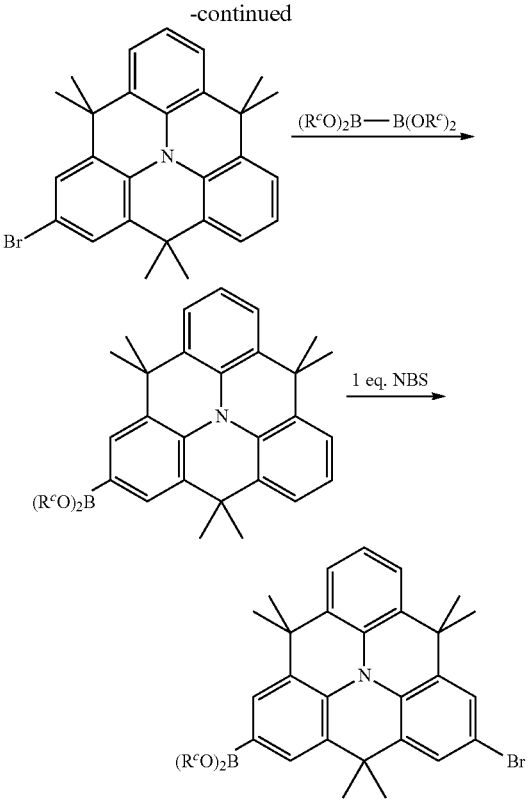

The compounds with boron ester groups can be subjected to a Suzuki coupling reaction. Scheme 3 depicts the formation of a triangulene trimer by a Suzuki coupling reaction followed by a trimerization to obtain the corresponding nonamer by Ni(0)-mediated aryl-aryl bond formation.

If the coupling reaction results in compounds of the formula (I) with halogenated terminal repeat units, the halogen groups can be subjected to a further functionalization. In a preferred embodiment, this further functionalization is performed as a one pot reaction together with the formation of the skeleton of the compound (I) by one of the afore-mentioned coupling reactions. Thus, if e.g. the Ni(0)-mediated aryl-aryl bond formation is quenched with a proton donor, at least a part of the halogen groups are replaced by a hydrogen atom. Suitable proton donors are Broenstedt acids, preferably hydrochloric acid or sulphuric acid. In the trimerization to obtain the nonamer according to scheme 3, a Broenstedt acid has been added as the final reaction step and consequently the terminal triangulene units are not substituted by bromine atoms. If in an alternative variant an unsubstituted or substituted aryl halide is added to the Ni(0)-mediated aryl-aryl bond formation, at least a part of the halogen groups are replaced by unsubstituted or substituted aryl groups. In the polymerization to obtain a polymeric compound of the formula (I) according to scheme 4, bromobenzene has been added as the final reaction step and consequently the obtained polymer bears terminal phenyl groups.

Scheme 3:
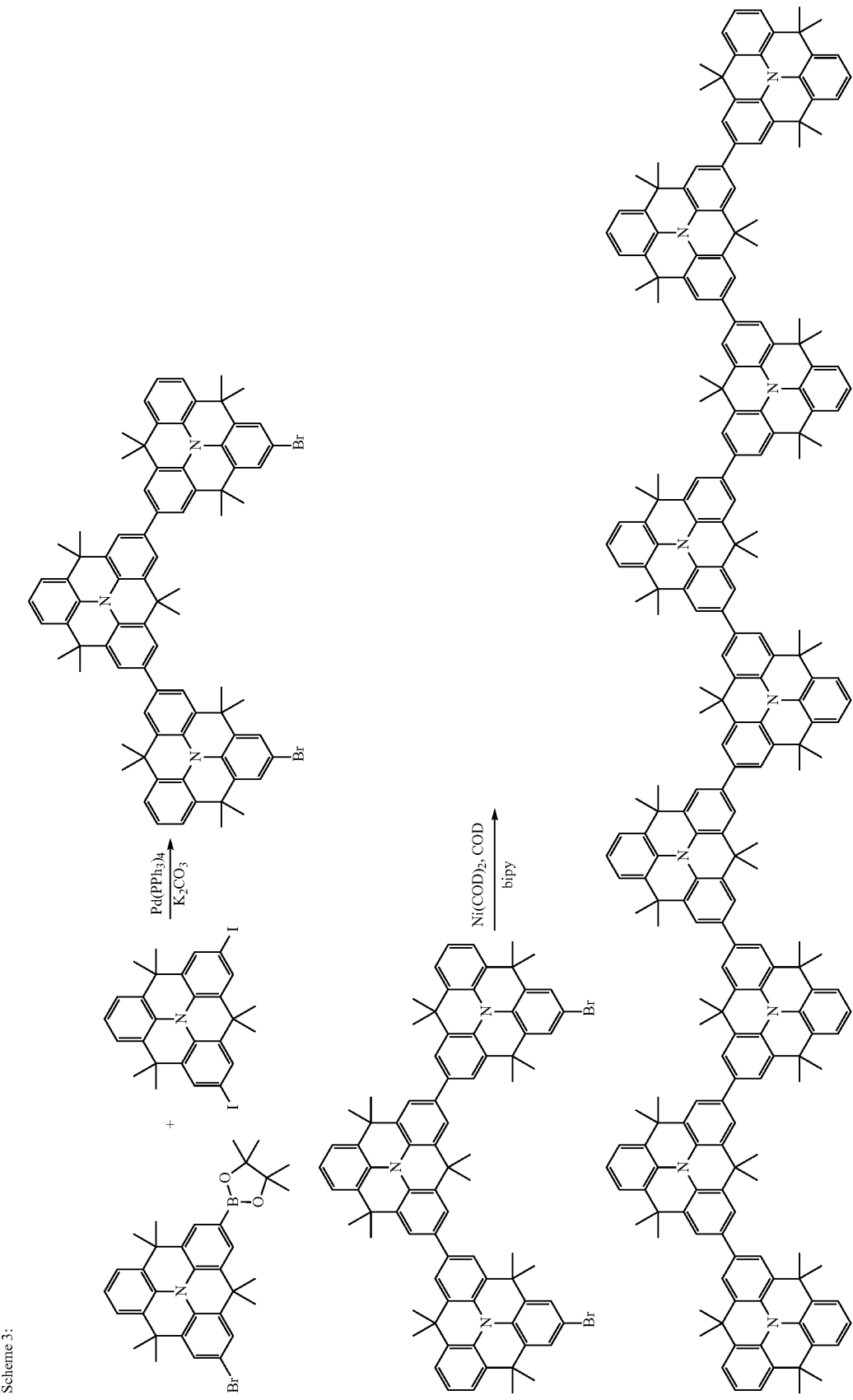

Scheme 4 depicts the formation of a triangulene polymer by a Ni(0)-mediated aryl-aryl bond formation, where n is the number of repeating units and preferably in a range of from 20 to 75.

Scheme 4:

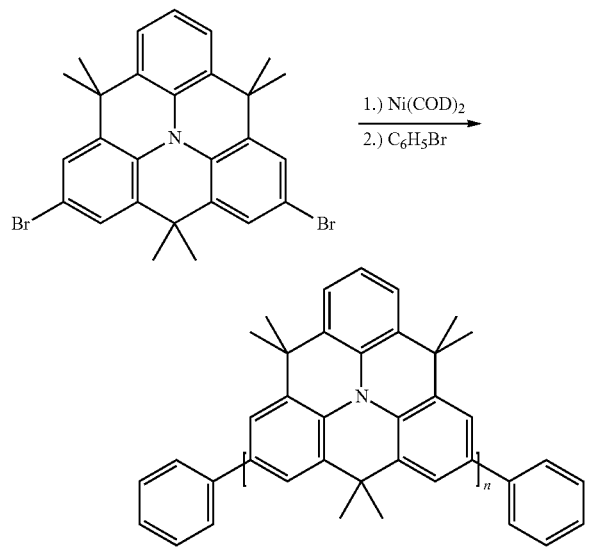

The compounds of the formula (I) can be isolated by methods known in the art, such as column chromatography.

The compounds of the formula (I) are in particular suitable as organic semiconductors, in particular p-semiconductors.

Preferably, the compounds of the formula (I) are employed for the production of a dye-sensitized or a Perovskite-based photoelectric conversion device.

A preferred embodiment is a dye-sensitized photoelectric conversion device, comprising:
  an electrically conductive layer being part of or forming the working electrode (anode),
  a photosensitive layer comprising a semiconductive metal oxide and a chromophoric substance,
  a charge transfer layer comprising at least one compound of the formula (I),
  an electrically conductive layer being part of or forming the counter electrode (cathode).

A further preferred embodiment is a Perovskite-based photoelectric conversion device, comprising:
  an electrically conductive layer being part of or forming the working electrode (anode),
  a photosensitive layer comprising a Perovskite absorber material,
  a charge transfer layer comprising at least one compound of the formula (I),
  an electrically conductive layer being part of or forming the counter electrode (cathode).

The dye-sensitized photoelectric conversion device of the invention may be in form of a liquid or a solid state dye-sensitized photoelectric conversion device. Preferably, the dye-sensitized photoelectric conversion device of the invention is in form of a solid state device, in particular a solid state dye-sensitized solar cell (sDSSC).

The Perovskite-based photoelectric conversion device of the invention is generally in form of a solid state device. In a first embodiment, the photosensitive layer of the Perovskite-based photoelectric conversion device comprising a Perovskite absorber material and at least one semiconductive metal oxide. Suitable semiconductive metal oxides are those described in the following for the dye-sensitized photoelectric conversion devices, in particular $TiO_2$. Devices according to this first embodiment are described in H.-S. Kim et al., Scientific Reports, 2: 59, DOI: 10.1038/srep00591. In a second embodiment, the photosensitive layer of the Perovskite-based photoelectric conversion comprising a Perovskite absorber material and a carrier material that does not act as a n-type oxide, in particular $Al_2O_3$. Devices according to this second embodiment are described in M. M. Lee et al describe in Sciencexpress, 4 Oct. 2012, 10.1126/science.1228604.

In the context of the present invention "layer" does not necessarily imply that each layer is physically strictly separated from the other layers. In fact, the layers may permeate into each other. For instance, the material of which the charge transfer layer is composed generally permeates into the photosensitive layer and comes into close contact with the semiconductive metal oxide and the dye, so that a fast charge transfer is possible.

A suitable process for producing a dye-sensitized or Perovskite-based photoelectric conversion device comprises the following steps:
i) providing an electrically conductive layer;
ii) optionally depositing an undercoating layer thereon,
iii) depositing a photosensitive layer on the electrically conductive layer obtained in step i) or, if present, the undercoating layer obtained in step ii); semiconductive
iv) depositing a charge transfer layer on the photosensitive layer obtained in step iii); and
v) depositing a counter electrically conductive layer on the charge transfer layer obtained in step iv).

In case of a dye-sensitized photoelectric conversion device the photosensitive layer produced in step iii) comprises a semiconductive metal oxide sensitized by a chromophoric substance. In case of a Perovskite-based photoelectric conversion device the photosensitive layer produced in step iii) comprises a Perovskite absorber and a semiconductive metal oxide or a carrier material that does not act as an n-type oxide.

The electrically conductive layer and/or the counter electrically conductive layer may be disposed on a substrate (also called support or carrier) to improve the strength of the photoelectric conversion device. In the present invention, a layer composed of the electrically conductive layer and a substrate on which it is disposed is referred to as conductive support. A layer composed of the counter electrically conductive layer and a substrate on which it is optionally disposed is referred to as counter electrode. Preferably, the electrically conductive layer and the substrate on which it is optionally disposed are transparent. The counter electrically conductive layer and optionally also the support on which this is optionally disposed may be transparent too, but this is not critical.

Each layer comprised in the photoelectric conversion device obtained in the method of the present invention will be explained in detail below.

(A) Electrically Conductive Layer [Step (i)]

The electrically conductive layer is either as such stable enough to support the remaining layers, or the electrically conductive material forming the electrically conductive layer is disposed on a substrate (also called support or carrier). Preferably, the electrically conductive material forming the electrically conductive layer is disposed on a substrate. The combination of electrically conductive material disposed on a substrate is called in the following "conductive support".

In the first case, the electrically conductive layer is preferably made of a material that has a sufficient strength and that can sufficiently seal the photoelectric conversion device, for example, a metal such as platinum, gold, silver, copper, zinc, titanium, aluminum and an alloy composed thereof.

In the second case, the substrate on which the electrically conductive layer containing an electrically conductive material is generally disposed opposite of the photosensitive layer, so that the electrically conductive layer is in direct contact with the photosensitive layer.

Preferred examples of the electrically conductive material include: metals such as platinum, gold, silver, copper, zinc, titanium, aluminum, indium and alloys composed thereof; carbon, especially in the form of carbon nano tubes; and electrically conductive metal oxides, especially transparent conductive oxides (TCO), such as for example indium-tin composite oxides, tin oxides doped with fluorine, antimony or indium and zinc oxide doped with aluminum. In case of metals, these are generally used in form of thin films, so that they form a sufficiently transparent layer. More preferably, the electrically conductive material is selected from transparent conductive oxides (TCO). Among these, tin oxides doped with fluorine, antimony or indium and indium-tin oxide (ITO) are preferred, more preferred being tin oxides doped with fluorine, antimony or indium and specifically preferred being tin oxides doped with fluorine. Specifically, the tin oxide is $SnO_2$.

The electrically conductive layer preferably has a thickness of 0.02 to 10 μM and more preferably from 0.1 to 1 μm.

Generally, light will be irradiated from the side of the electrically conductive layer (and not from the counter electrically conductive layer side). Thus, as already mentioned, it is preferred that the support which carries the electrically conductive layer and preferably the conductive support as a whole is substantially transparent. Herein, the term "substantially transparent" means that the light transmittance is 50% or more to a light in visible region to near infrared region (400 to 1000 nm). The light transmittance is preferably 60% or more, more preferably 70% or more and in particular 80% or more. The conductive support particularly preferably has high light transmittance to a light that the photosensitive layer has sensitivity to.

The substrate may be made of a glass, such as soda glass (that is excellent in strength) and non-alkali glass (that is not affected by alkaline elution). Alternatively, a transparent polymer film may be used as substrate. Used as the materials for the polymer film may be tetraacetyl cellulose (TAC), polyethylene terephthalate (PET), polyethylene naphthalate (PEN), syndiotactic polystyrene (SPS), polyphenylenesulfide (PPS), polycarbonate (PC), polyarylate (PAr), polysulfone (PSF), polyestersulfone (PES), polyimide (PI), polyetherimide (PEI), cyclic polyolefin, brominated phenoxy resin, and the like.

The conductive support is preferably prepared by disposing the electrically conductive material on the substrate by means of liquid coating or vapor deposition.

The amount of the electrically conductive material to be disposed on the substrate is chosen so that a sufficient transparency is secured. The suitable amount depends on the conductive material and the substrate used and will be determined for the single cases. For instance, in case of TCOs as conductive material and glass as substrate the amount may vary from 0.01 to 100 g per 1 $m^2$.

It is preferable that a metal lead is used to reduce the resistance of the conductive support. The metal lead is preferably made of a metal such as platinum, gold, nickel, titanium, aluminum, copper, silver, etc. It is preferable that the metal lead is provided on the substrate by a vapor deposition method, a sputtering method or the like, the electrically conductive layer being disposed thereon. The reduction in incident light quantity owing to the metal lead is limited to preferably 10% or less, more preferably 1 to 5% or less.

(B) Undercoating Layer ("Buffering Layer") [Optional Step (ii)]

The layer obtained in step (i) may be coated with a buffering layer. The purpose is to avoid a direct contact of the charge transfer layer with the electrically conductive layer and thus to prevent short-circuits, particularly in the case where the charge transfer layer is a solid hole-transporting material.

This "undercoating" or buffering layer material is preferably a metal oxide. The metal oxide is preferably selected from a titanium, tin, zinc, iron, tungsten, vanadium or niobium oxide, such as $TiO_2$, $SnO_2$, $Fe_2O_3$, $WO_3$, $ZnO$, $V_2O_5$ or $Nb_2O_5$, and is more preferably $TiO_2$.

The undercoating layer may be disposed e.g. by a spray-pyrolysis method as described for example in Electrochim. Acta, 40, 643 to 652 (1995), or a sputtering method as described for example in Thin Solid Films 445, 251-258 (2003), Suf. Coat. Technol. 200, 967 to 971 (2005) or Coord. Chem. Rev. 248 (2004), 1479.

The thickness of the undercoating layer is preferably 5 to 1000 nm, more preferably 10 to 500 nm and in particular 10 to 200 nm.

(C) Photosensitive Layer [Step (iii)]

In a first embodiment, the photosensitive layer contains the semiconductive metal oxide sensitized with a chromophoric substance (also denoted as dye or photosensitive dye). The dye-sensitized semiconductive metal oxide acts as a photosensitive substance to absorb light and conduct charge separation, thereby generating electrons. As is generally known, thin layers or films of metal oxides are useful solid semiconductive materials (n-semiconductors). However, due to their large band gap they do not absorb in the visible range of the electromagnetic spectrum, but rather in the UV region. Thus, for the use in photoelectric conversion devices for solar cells, they have to be sensitized with a dye that absorbs in the range of about 300 to 2000 nm. In the photosensitive layer, the dye molecules absorb photons of the immersive light which have a sufficient energy. This creates an excited state of the dye molecules which inject an electron into the conduction band of the semiconductive metal oxide. The semiconductive metal oxide receives and conveys the electrons to the electrically conductive layer and thus to the working electrode (see below).

In a second embodiment, the photosensitive layer comprises a Perovskite absorber and a semiconductive metal oxide or a carrier material that does not act as an n-type oxide.

(1) Semiconductive Metal Oxide

An n-type semiconductor is preferably used in the present invention, in which conduction band electrons act as a carrier under photo-excitation condition to provide anode current.

Suitable semiconductive metal oxides are all metal oxides known to be useful on organic solar cells. They include: oxides of titanium, tin, zinc, iron, tungsten, zirconium, hafnium, strontium, indium, cerium, yttrium, lanthanum, vanadium, caesium, niobium or tantalum. Further, composite semiconductors such as $M^1_xM^2_yO_z$ may be used in the present invention, wherein M, $M^1$ and $M^2$ independently represent a metal atom, O represents an oxygen atom, and x, y and z represent numbers combined with each other to form a neutral molecule. Examples are $TiO_2$, $SnO_2$, $Fe_2O_3$, $WO_3$, $ZnO$, $Nb_2O_5$, $SrTiO_3$, $Ta_2O_5$, $Cs_2O$, zinc stannate, complex oxides of the Perovskite type, such as barium titanate, and binary and ternary iron oxides.

Preferred semiconductive metal oxides are selected from $TiO_2$, $SnO_2$, $Fe_2O_3$, $WO_3$, $ZnO$, $Nb_2O_5$, and $SrTiO_3$. Of these semiconductors, more preferred are $TiO_2$, $SnO_2$, $ZnO$ and mixtures thereof. Even more preferred are $TiO_2$, ZnO and mixtures thereof, particularly preferred being $TiO_2$.

The metal oxides are preferably present in amorphous or nanocrystalline form. More preferably, they are present as nanocrystalline porous layers. Such layers have a big surface on which a large number of dye molecules can be absorbed, thus resulting in a high absorption of immersing light. The metal oxide layers may also be present in a structured form, such as nanorods. Nanorods offer the advantage of high electron mobility and an improved filling of the pores with the dye.

If more than one metal oxide is used, the two or more metal oxides can be applied as mixtures when the photosensitive layer is formed. Alternatively, a layer of a metal oxide may be coated with one or more metal oxides different therefrom.

The metal oxides may also be present as a layer on a semiconductor different therefrom, such as GaP, ZnP or ZnS.

$TiO_2$ and ZnO used in the present invention are preferably in anatase-type crystal structure, which in turn is preferably nanocrystalline.

The semiconductor may or may not comprise a dopant to increase the electron conductivity thereof. Preferred dopants are metal compounds such as metals, metal salts and metal chalcogenides.

In the photosensitive layer the semiconductive metal oxide layer is preferably porous, particularly preferably nanoporous and specifically mesoporous.

Porous material is characterized by a porous, non-smooth surface. Porosity is a measure of the void spaces in a material, and is a fraction of the volume of voids over the total volume. Nanoporous material has pores with a diameter in the nanometer range, i.e. ca. from 0.2 nm to 1000 nm, preferably from 0.2 to 100 nm. Mesoporous material is a specific form of nanoporous material having pores with a diameter of from 2 to 50 nm. "Diameter" in this context refers to the largest dimension of the pores. The pores' diameter can be determined by several porosimetry methods, such as optical methods, imbibition methods, water evaporation method, mercury intrusion porosimetry or gas expansion method.

The particle size of the semiconductive metal oxide used for producing the semiconductive metal oxide layer is generally in the nm to μm range. The mean size of primary semiconductor particles, which is obtained from a diameter of a circle equivalent to a projected area thereof, is preferably 200 nm or less, e.g. 5 to 200 nm, more preferably 100 nm or less, e.g. 5 to 100 nm or 8 to 100 nm.

Two or more of the semiconductive metal oxides having a different particle size distribution may be mixed in the preparation of the photosensitive layer. In this case, the average particle size of the smaller particles is preferably 25 nm or less, more preferably 10 nm or less. To improve a light-capturing rate of the photoelectric conversion device by scattering rays of incident light, the semiconductive metal oxides having a large particle size, e.g. approximately 100 to 300 nm in diameter, may be used for the photosensitive layer.

Preferred as a method for producing the semiconductive metal oxides are: sol-gel methods described for example in Materia, Vol. 35, No. 9, Page 1012 to 1018 (1996). The method developed by Degussa Company, which comprises preparing oxides by subjecting chlorides to a high temperature hydrolysis in an oxyhydrogen salt, is also preferred.

In the case of using titanium oxide as the semiconductive metal oxides, the above-mentioned sol-gel methods, gel-sol methods, high temperature hydrolysis methods are preferably used. Of the sol-gel methods, also preferred are such that described in Barbe et al., Journal of American Ceramic Society, Vol. 80, No. 12, Page 3157 to 3171 (1997) and Burnside et al, Chemistry of Materials, Vol. 10, No. 9, Page 2419 to 2425 (1998).

The semiconductive metal oxides may be applied onto the layer obtained in step (i) or, if carried out, step (ii), by: a method where the layer obtained in step (i) or (ii) is coated with a dispersion or a colloidal solution containing the particles; the above-mentioned sol-gel method; etc. A wet type layer formation method is relatively advantageous for the mass production of the photoelectric conversion device, for improving the properties of the semiconductive metal oxide dispersion, and for improving the adaptability of the layer obtained in step (i) or (ii), etc. As such a wet type layer formation method, coating methods, printing methods, electrolytic deposition methods and electrodeposition techniques are typical examples. Further, the semiconductive metal oxide layer may be disposed by: oxidizing a metal; an LPD (liquid phase deposition) method where a metal solution is subjected to ligand exchange, etc.; a sputtering method; a PVD (physical vapor deposition) method; a CVD (chemical vapour deposition) method; or an SPD (spray pyrolysis deposition) method where a thermal decomposition-type metal oxide precursor is sprayed on a heated substrate to generate a metal oxide.

The dispersion containing the semiconductive metal oxides may be prepared by: the sol-gel methods mentioned above; crushing the semiconductor in a mortar; dispersing the semiconductor while grinding it in a mill; synthesizing and precipitating the semi-conductive metal oxides in a solvent; etc.

As a dispersion solvent, water or organic solvents such as methanol, ethanol, isopropyl alcohol, citronellol, terpineol, dichloromethane, acetone, acetonitrile, ethyl acetate, etc., mixtures thereof and mixtures of one or more of these organic solvents with water may be used. A polymer such as polyethylene glycol, hydroxyethylcellulose and carboxymethylcellulose, a surfactant, an acid, a chelating agent, etc. may be used as a dispersing agent, if necessary. In particular, polyethylene glycol may be added to the dispersion because the viscosity of the dispersion and the porosity of the semiconductive metal oxide layer can be controlled by changing the molecular weight of the polyethylene glycol, and the semiconductive metal oxide layer containing polyethylene glycol is hardly peeled off.

Preferred coating methods include e.g. roller methods and dip methods for applying the semi-conductive metal oxide, and e.g. air-knife methods and blade methods for calibrating the layer. Further, preferable as a method where the application and calibration can be performed at the same time are wire-bar methods, slide-hopper methods, e.g. such as described in U.S. Pat. No. 2,761,791, extrusion methods, curtain methods, etc. Furthermore, spin methods and spray methods may be used. As to wet type printing methods relief printing, offset printing, gravure printing, intaglio printing, gum printing, screen printing, etc. are preferred. A preferable layer formation method may be selected from these methods in accordance with the viscosity of the dispersion and the desired wet thickness.

As already mentioned, the semiconductive metal oxide layer is not limited to a single layer. Dispersions each comprising the semiconductive metal oxides having a different particle size may be subjected to a multi-layer coating. Further, dispersions each containing different kinds of semiconductive metal oxides, binder or additives may be subjected to a multi-layer coating. The multi-layer coating is also effectively used in case the thickness of a single layer is insufficient.

Generally, with increasing thickness of the semiconductive metal oxide layer, which equals the thickness of the photosensitive layer, the amount of the dye incorporated therein per unit of projected area increases resulting in a higher light capturing rate. However, because the diffusion distances of the generated electrons also increase, higher loss rates owing to recombination of the electric charges is to be expected. Moreover, customarily used dyes such as phthalocyanins and porphyrins have a high absorption rates, so that thin layers or films of the metal oxide are sufficient. Consequently, the preferable thickness of the semiconductive metal oxide layer is 0.1 to 100 μm, more preferably 0.1 to 50 μm, even more preferably 0.1 to 30 μm, in particular 0.1 to 20 μm and specifically 0.5 to 3 μm.

A coating amount of the semiconductive metal oxides per 1 m$^2$ of the substrate is preferably 0.5 to 100 g, more preferably 3 to 50 g.

After applying the semiconductive metal oxide(s) onto the layer obtained in step (i) or (ii), the obtained product is preferably subjected to a heat treatment (sintering step), to electronically contact the metal oxide particles with each other and to increase the coating strength and the adherence thereof with the layer below. The heating temperature is preferably 40 to 700° C., more preferably 100 to 600° C. The heating time is preferably 10 minutes to 10 hours.

However, in case the electrically conductive layer contains a thermosensitive material having a low melting point or softening point such as a polymer film, the product obtained after the application of the semiconductive metal oxide is preferably not subjected to a high temperature treatment because this may damage such a substrate. In this case, the heat treatment is preferably carried out at a temperature as low as possible, for example, 50 to 350° C. In this case, the semiconductive metal oxide is preferably one with smaller particles, in particular having a medium particle size of 5 nm or less. Alternatively, a mineral acid or a metal oxide precursor can be heat-treated at such a low temperature.

Further, the heat treatment may be carried out while applying an ultraviolet radiation, an infrared radiation, a microwave radiation, an electric field, an ultrasonic wave, etc. to the semiconductive metal oxides, in order to reduce the heating temperature. To remove unnecessary organic compounds, etc., the heat treatment is preferably carried out in combination with evacuation, oxygen plasma treatment, washing with pure water, a solvent or a gas, etc.

If desired, it is possible to form a blocking layer on the layer of the semiconductive metal oxide before sensitizing it with a dye in order to improve the performance of the semiconductive metal oxide layer. Such a blocking layer is usually introduced after the aforementioned heat treatment. An example of forming a blocking layer is immersing the semiconductive metal oxide layer into a solution of metal alkoxides such as titanium ethoxide, titanium isopropoxide or titanium butoxide, chlorides such as titanium chloride, tin chloride or zinc chloride, nitrides or sulfides and then drying or sintering the substrate. For instance, the blocking layer is made of a metal oxide, e.g. $TiO_2$, $SiO_2$, $Al_2O_3$, $ZrO_2$, MgO, $SnO_2$, ZnO, $Eu_2O_3$, $Nb_2O_5$ or combinations thereof, $TiCl_4$, or a polymer, e.g. poly(phenylene oxide-co-2-allylphenylene oxide) or poly(methylsiloxane). Details of the preparation of such layers are described in, for example, Electrochimica Acta 40, 643, 1995; J. Am. Chem. Soc 125, 475, 2003; Chem. Lett. 35, 252, 2006; J. Phys. Chem. B, 110, 1991, 2006. Preferably, $TiCl_4$ is used. The blocking layer is usually dense and compact, and is usually thinner than the semiconductive metal oxide layer.

As already said, it is preferable that the semiconductive metal oxide layer has a large surface area to adsorb a large number of dye molecules. The surface area of the semiconductive metal oxide layer is preferably 10 times or more, more preferably 100 times or more higher than its projected area.

(2) Dye

The dye used as chromophoric substance for the photosensitive layer is not particularly limited if it can absorb light particularly in the visible region and/or near infrared region (especially from ca. 300 to 2000 nm) and can sensitize the semiconductive metal oxide. Examples are metal complex dyes (see for example U.S. Pat. No. 4,927,721, U.S. Pat. No. 5,350,644, EP-A-1176646, Nature 353, 1991, 737-740, Nature 395, 1998, 583-585, U.S. Pat. No. 5,463,057, U.S. Pat. No. 5,525,440, U.S. Pat. No. 6,245,988, WO 98/50393), indoline dyes (see for example (Adv. Mater. 2005, 17, 813), oxazine dyes (see for example U.S. Pat. No. 6,359,211), thiazine dyes (see for example U.S. Pat. No. 6,359,211), acridine dyes (see for example U.S. Pat. No. 6,359,211), prophyrin dyes, methine dyes (preferably polymethine dyes such as cyanine dyes, merocyanine dyes, squalilium dyes, etc; see for example U.S. Pat. No. 6,359,211, EP 892411, EP 911841, EP 991092, WO 2009/109499) and rylene dyes (see for example JP-A-10-189065, JP 2000-243463, JP 2001-093589, JP 2000-100484, JP 10-334954, New J. Chem. 26, 2002, 1155-1160 and in particular DE-A-10 2005 053 995 and WO 2007/054470).

To make the photoelectric conversion wave range of the photoelectric conversion device larger, and to increase the photoelectric conversion efficiency, two or more kinds of the dyes may be used as a mixture or in combination thereof. In the case of using two or more kinds of the dyes, the kinds and the ratio of the dyes may be selected in accordance with the wave range and the strength distribution of the light source.

For instance the absorption of the rylene dyes depends on the extent of the conjugated system. The rylene derivatives of DE-A-10 2005 053 995 have an absorption of from 400 nm (perrylene derivatives I) to 900 nm (quaterrylene derivatives I). Terrylenebased dyes absorb from about 400 to 800 nm. In order to obtain absorption over a range of the electromagnetic waves as large as possible it is thus advantageous to use a mixture of rylene dyes with different absorption maxima.

The dye preferably has an interlocking or anchor group, which can interact or adsorb to the surface of the semiconductive metal oxides. Preferred interlocking groups include acidic groups such as —COOH, —OH, —$SO_3H$, —P(O)(OH)$_2$ and —OP(O)(OH)$_2$, and π-conductive chelating groups such as oxime group, dioxime group, hydroxyquinoline group, salicylate group and α-ketoenolate group. Anhydride groups are also suitable as they react in situ to carboxylic groups. Among them, preferred are acidic groups, particularly preferred are —COOH, —P(O)(OH)$_2$ and —OP(O)(OH)$_2$. The interlocking group may form a salt with an alkaline metal, etc. or an intramolecular salt. In the case of polymethine dyes, an acidic group such as squarylium ring group or croconium ring group formed by the methine chain may act as the interlocking group.

Preferably, the dye has on the distal end (i.e. the end of the dye molecule opposite the anchor group) one or more electron donating groups which facilitate the regeneration of the dye after having donated an electron to the semiconductive metal oxide and which optionally also prevent recombination with the donated electrons.

The dye may be adsorbed to the semiconductive metal oxides by bringing these components into contact with each other, e.g. by soaking the product obtained after the application of the semiconductive metal oxide layer in a dye adsorption solution, or by applying the dye adsorption solution to the semiconductive metal oxide layer. In the former case, a soaking method, a dipping method, a roller method, an air-knife method, etc. may be used. In the soaking method. The dye may be adsorbed at room temperature, or under reflux while heating as described in JP 7249790. As an applying method of the latter case, a wire-bar method, a slide-hopper method, an extrusion method, a curtain method, a spin method, a spray method, etc. may be used. Further, the dye may be applied to the semiconductive metal oxide layer by an ink-jet method onto an image, thereby providing a photoelectric conversion surface having a shape of the image.

These methods can be used also in the case where the dye is adsorbed on the semiconductive metal oxide while the semiconductive metal oxide is treated with an additive, e.g. at least one hydroxamic acid or its salt, as described in WO 2012/001628 A1. Thus, the dye adsorption solution may contain the additive, in particular one or more hydroxamic acids or their salts. Preferably, the dye, e.g. in the form of a suspension or solution, is brought into contact with the semiconductive metal-oxide when this is freshly sintered, i.e. still warm. The contact time should be sufficiently long to allow absorption of the dye to the surface of the metal oxide. The contact time is typically from 0.5 to 24 h.

If more than one dye is to be applied, the application of the two or more dyes can be carried out simultaneously, e.g. by using a mixture of two or more dyes, or subsequently by applying one dye after the other.

The dye may also be applied in mixture with the at least one hydroxamic acid or its salt. Additionally or alternatively the dye may be applied in combination with the charge transfer material.

The dye unadsorbed on the semiconductive metal oxide layer is preferably removed by washing immediately after the dye adsorption process. The washing is preferably carried out by a wet-type washing bath with a polar solvent, in particular a polar organic solvent, for example acetonitrile or an alcohol solvent.

The amount of the dye adsorbed on the semiconductive metal oxides is preferably 0.01 to 1 mmol per 1 g of the semiconductive metal oxides. Such an adsorption amount of the dye usually effects a sufficient sensitization to the semiconductors. Too small an amount of the dye results in insufficient sensitization effect. On the other hand, unadsorbed dye may float on the semiconductive metal oxides resulting in a reduction of the sensitization effect.

To increase the adsorption amount of the dye the semiconductive metal oxide layer may be subjected to a heat treatment before the dye is adsorbed thereon. After the heat treatment, it is preferable that the dye is quickly adsorbed on the semiconductive metal oxide layer having a temperature of 60 to 150° C. before the layer is cooled to room temperature, to prevent water from adsorbing onto the semiconductive metal oxide layer.

(3) Perovskite Absorber Material

The Perovskite absorber material is preferably an organometallic halide compound. Preferred are compounds of the formula $(R^d NH_3)PbX^a{}_3$, wherein $R^d$ is $C_1$-$C_4$ alkyl and $X^a$ is Cl, Br or I. Especially preferred are $(CH_3NH_3)PbI_3$, $(CH_3CH_2NH_3)PbI_3$, $(CH_3NH_3)PbI_2Cl$ and $(CH_3CH_2NH_3)PbI_2Cl$.

(4) Non-Semiconductive Carrier Material

Preferred as a non-semiconductive carrier material is $Al_2O_3$.

(5) Passivating Material

In order to prevent recombination of the electrons in the semiconductive metal oxide with the charge transfer layer a passivating layer can be provided on the semiconductive metal oxide. The passivating layer can be provided before the absorption of the dye and also of the hydroxamic acid or its salt, or after the dye absorption process and the treatment with the hydroxamic acid or its salt. Suitable passivating materials are aluminium salts, $Al_2O_3$, silanes, such as $CH_3SiCl_3$, metal organic complexes, especially $Al^3$ complexes, 4-tert-butyl pyridines, MgO, 4-guanidino butyric acid and hexadecyl malonic acid. The passivating layer is preferably very thin.

(D) Charge Transfer Layer [Step (iv)]

The charge transfer layer replenishes electrons to the oxidized dye. According to a preferred embodiment of the invention, the charge transfer layer comprises at least one compound of the formula (I) as hole-transporting material (p-semiconductor). With regard to suitable and preferred compounds of the formula (I), reference is made to the aforementioned suitable and preferred embodiments of the compound of the formula (I).

The charge transfer layer may contain at least one further hole-transporting material different from the compound of the formula (I).

Suitable additional hole-transporting materials are inorganic hole-transporting materials, organic hole-transporting materials or a combination thereof. Preferably, the additional hole-transporting material is in the solid state. Those compounds are known to a person skilled in the art.

In a preferred embodiment, the dye-sensitized or Perovskite-based photoelectric conversion device according to the invention does not comprising a further hole-transporting material in addition to at least one compound of the formula (I).

Method for Forming the Charge Transfer Layer

The charge transfer layer may be provided e.g. by one of the following two methods. According to a first method, the counter electrode is placed on the photosensitive layer first and then the material of the charge transfer layer is applied in the liquid state to penetrate the gap therebetween. According to a second method, the charge transfer layer is first directly disposed on the photosensitive layer and the counter electrode is disposed afterwards.

In the case of providing a wet charge transfer layer by the second method, the wet charge transfer layer is applied to the photosensitive layer, the counter electrode is disposed on the wet charge transfer layer without drying it and edges thereof are subjected to a treatment for preventing liquid-leakage, if necessary. In the case of providing a gel charge transfer layer by the second method, the charge transfer material may be applied in the liquid state and gelled by polymerization, etc. In this case, the counter electrode may be disposed on the charge transfer layer before or after drying and fixing the charge transfer layer.

The charge transfer layer may be disposed e.g. by a roller method, a dip method, an air-knife method, an extrusion method, a slide-hopper method, a wire-bar method, a spin method, a spray method, a cast method or a printing method. Suitable methods are similar to those of forming the semiconductive metal oxide layer or adsorbing a dye to the semiconductor, mentioned above.

If the charge transfer layer is composed of at least one solid electrolyte, the solid hole transporting material, etc. may be formed by a dry film-forming method such as a physical vacuum deposition method or a CVD method, followed by disposing the counter electrode thereon. The hole-transporting material may be made to penetrate into the photosensitive layer by a vacuum deposition method, a cast method, a coating method, a spin-coating method, a soaking method, an electrolytic polymerization method, a photo-polymerization method, a combination of these methods, etc.

(E) Counter Electrode [Step (v)]

As already said, the counter electrode is the counter electrically conductive layer, which is optionally supported by a substrate as defined above. Examples of the electrically conductive material used for the counter electrically conductive layer include: metals such as platinum, gold, silver, copper, aluminum, magnesium and indium; mixtures and alloys thereof, especially of aluminum and silver; carbon; electrically conductive metal oxides such as indium-tin composite oxides and fluorine-doped tin oxides. Among them, preferred are platinum, gold, silver, copper, aluminum and magnesium, and particularly preferred silver or gold. Specifically, silver is used. Suitable electrodes are moreover mixed inorganic/organic electrodes and polylayer electrodes, such as LiF/Al electrodes. Suitable electrodes are described for example in WO 02/101838 (especially pp 18-20)

The substrate of the counter electrode is preferably made of a glass or a plastic to be coated or vapor-deposited with the electrically conductive material. The counter electrically conductive layer preferably has a thickness of 3 nm to 10 µm, although the thickness is not particularly limited.

Light may be irradiated from any one or both sides of the electrically conductive layer provided in step (i) and the counter electrode provided in step (v), so that at least one of them should be substantially transparent to have light reached to the photosensitive layer. From a viewpoint of improving electric generation efficiency, it is preferable that the electrically conductive layer provided in step (i) is substantially transparent to incident light. In this case, the counter electrode preferably has a light-reflective property. Such a counter electrode may be composed of a glass or a plastic having a vapor-deposited layer of metal or electrically conductive oxide, or metal thin film. This type of device, which is also called "concentrator", is described for example in WO 02/101838 (especially on pp 23-24).

The counter electrode may be disposed by applying metal-plating or vapor-depositing (physical vapor deposition (PVD), CVD, etc.) the electrically conductive material directly onto the charge transfer layer. Similar as with the conductive support, it is preferable that a metal lead is used to reduce the resistance of the counter electrode. The metal lead is particularly preferably used for a transparent counter electrode. Preferable embodiments of the metal lead used for the counter electrode are the same as those of the metal lead used for the conductive layer mentioned above.

(F) Others

At least one further functional layer, such as a protective layer and a reflection-preventing layer, may be disposed on any one or both of the conductive layers and/or the counter electrode. The functional layers may be disposed by a method selected in accordance with the materials used therefor, such as a coating method, a vapor-deposition method and a sticking method.

(G) Interior Structure of Photoelectric Conversion Device

As described above, the photoelectric conversion device may have various interior structures according to the desired end use. The structures are classified into two major forms, a structure allowing light incidence from both faces, and a structure allowing it from only one face. In the first case, the photosensitive layer, the charge transfer layer and the other optionally present layers are disposed between a transparent electrically conductive layer and a transparent counter electrically conductive layer. This structure allows light incidence from both faces of the device. In the second case, one of the transparent electrically conductive layer and the transparent counter electrically conductive layer is transparent, while the other is not. As a matter of course, if the electrically conductive layer is transparent, light immerses from the electrically conductive layer side, while in case of the counter electrically conductive layer being transparent, light immerses from the counter electrode side.

The invention further relates to a photoelectric conversion device obtainable by the process of the invention.

Preferably, the photoelectric conversion device of the invention comprises

I) an electrically conductive layer;
II) optionally an undercoating layer,
III) a photosensitive layer;
IV) a charge transfer layer, comprising at least one compound of the formula (I); and
V) a counter electrically conductive layer.

Photoelectric Cell

The present invention also relates to a photoelectric cell, preferably a solar cell, comprising the photoelectric conversion device as described above.

A photoelectric cell is constituted by connecting a photoelectric conversion device to an external circuit to electrically work or generate electricity in the external circuit. Such a photoelectric cell that has the charge transfer layer composed of ion conductive material is referred to as a photo-electrochemical cell. A photoelectric cell intended for power generation using solar light is referred to as a solar cell.

Thus, the photoelectric cell of the present invention is constituted by connecting the photoelectric conversion device of the present invention to an external circuit to electrically work or generate electricity in the external circuit. Preferably, the photoelectric cell is a solar cell, i.e. a cell intended for power generation using solar light.

The side face of the photoelectric cell is preferably sealed with a polymer or an adhesive agent, etc. to prevent deterioration and volatility of the content in the cell. The external circuit is connected to the conductive support and the counter electrode via a lead. Various known circuits may be used in the present invention.

In the case where the photoelectric conversion device of the present invention is applied to the solar cell, the interior structure of the solar cell may be essentially the same as that of the photoelectric conversion device mentioned above. The solar cell comprising the photoelectric conversion device of the present invention may have a known module structure. In generally known module structures of solar cells, the cell is placed on a substrate of metal, ceramic, etc. and covered with a coating resin, a protective glass, etc., whereby light is introduced from the opposite side of the substrate. The solar cell module may have a structure where the cells are placed on a substrate of a transparent material such as a tempered glass to introduce light from the transparent substrate side. Specifically, a super-straight type module structure, a substrate type module structure, a potting type module structure, substrate-integrated type module structure that is generally used in amorphous silicon solar cells, etc. are known as the solar cell module structures. The solar cell comprising the photoelectric conversion device of the present invention may have a module structure which is properly selected e.g. from the above structures which may be adapted in accordance with the respective requirements of a specific use.

The solar cell of the invention may be used in a tandem cell. Thus, the invention also relates to a tandem cell comprising the dye-sensitized solar cell of the invention and an organic solar cell.

Tandem cells are principally known and are described for example in WO 2009/013282. The tandem cells of the invention may be made as those described in WO 2009/013282, where the solar cell of the invention however replaces the dye-sensitized solar cell described in this reference.

The compounds of the formula (I) are advantageously suitable for organic field-effect transistors. They may be used, for example, for the production of integrated circuits (ICs), for which customary n-channel MOSFETs (metal oxide semiconductor field-effect transistors) have been used to date. These are then CMOS-like semiconductor units, for example for microprocessors, microcontrollers, static RAM and other digital logic circuits. For the production of semiconductor materials, the compounds of the formula (I) can be processed further by one of the following processes: printing (offset, flexo-graphic, gravure, screenprinting, inkjet, electrophotography), evaporation, laser transfer, photolithography, dropcasting. They are especially suitable for use in displays (specifically large-surface area and/or flexible displays), RFID tags, smart labels and sensors.

The compounds of the formula (I) are also advantageously suitable as electron conductors in organic field-effect transistors, organic solar cells and in organic light-emitting diodes. They are also particularly advantageous as an exciton transport material in excitonic solar cells.

The invention further provides organic field-effect transistors comprising a substrate with at least one gate structure, a source electrode and a drain electrode, and at least one compound of the formula (I) as defined above as a semiconductor.

The invention further provides substrates having a plurality of organic field-effect transistors, wherein at least some of the field-effect transistors comprise at least one compound of the formula (I) as defined above.

The invention also provides semiconductor units which comprise at least one such substrate.

A specific embodiment is a substrate with a pattern (topography) of organic field-effect transistors, each transistor comprising an organic semiconductor disposed on the substrate;
a gate structure for controlling the conductivity of the conductive channel; and
conductive source and drain electrodes at the two ends of the channel, the organic semiconductor consisting of at least one compound of the formula (I) or comprising a compound of the formula (I). In addition, the organic field-effect transistor generally comprises a dielectric.

A specific embodiment is a substrate with a pattern (topography) of organic field-effect transistors, each transistor comprising an organic semiconductor disposed on a buffer layer on a substrate;
a gate structure for controlling the conductivity of the conductive channel; and
conductive source and drain electrodes at the two ends of the channel, the organic semiconductor consisting of at least one compound of the formula (I) or comprising a compound of the formula (I). In addition, the organic field-effect transistor generally comprises a dielectric.

A further aspect of the invention is the provision of electronic components which comprise a plurality of semiconductor components, which may be n- and/or p-semiconductors. Examples of such components are field-effect transistors (FETs), bipolar junction transistors (BJTs), tunnel diodes, converters, light-emitting components, biological and chemical detectors or sensors, temperature-dependent detectors, photodetectors, such as polarization-sensitive photodetectors, gates, AND, NAND, NOT, OR, TOR and NOR gates, registers, switches, timer units, static or dynamic stores and other dynamic or sequential, logical or other digital components including programmable switches.

The compounds of the formula (I) are also particularly advantageously suitable for use in organic photovoltaics (OPVs). Preference is given to their use in solar cells which are characterized by diffusion of excited states (exciton diffusion). In this case, one or both of the semiconductor materials utilized is notable for a diffusion of excited states (exciton mobility). Also suitable is the combination of at least one semiconductor material which is characterized by diffusion of excited states with polymers which permit conduction of the excited states along the polymer chain. In the context of the invention, such solar cells are referred to as excitonic solar cells. The direct conversion of solar energy to electrical energy in solar cells is based on the internal photo effect of a semiconductor material, i.e. the generation of electron-hole pairs by absorption of photons and the separation of the negative and positive charge carriers at a p-n transition or a Schottky contact. An exciton can form, for example, when a photon penetrates into a semiconductor and excites an electron to transfer from the valence band into the conduction band. In order to generate current, the excited state generated by the absorbed photons must, however, reach a p-n transition in order to generate a hole and an electron which then flow to the anode and cathode. The photovoltage thus generated can bring about a photocurrent in an external circuit, through which the solar cell delivers its power. The semiconductor can absorb only those photons which have an energy which is greater than its band gap. The size of the semiconductor band gap thus determines the proportion of sunlight which can be converted to electrical energy. Solar cells consist normally of two absorbing materials with different band gaps in order to very effectively utilize the solar energy. Most organic semiconductors have exciton diffusion lengths of up to 10 nm. There is still a need here for organic semiconductors through which the excited state can be passed on over very large distances. It has now been found that, surprisingly, the compounds of the general formula (I) described above are particularly advantageously suitable for use in excitonic solar cells.

Organic solar cells generally have a layer structure and generally comprise at least the following layers: anode, photoactive layer and cathode. These layers are generally applied to a substrate suitable for this purpose. The structure of organic solar cells is described, for example, in US 2005/0098726 and US 2005/0224905.

The invention provides an organic solar cell which comprises a substrate with at least one cathode and at least one anode, and at least one compound of the general formula (I) as defined above as a photoactive material. The inventive organic solar cell comprises at least one photoactive region. A photoactive region may comprise two layers, each of which has a homogeneous composition and forms a flat donor-acceptor heterojunction. A photoactive region may also comprise a mixed layer and form a donor-acceptor heterojunction in the form of a donor-acceptor bulk heterojunction. Organic solar cells with photoactive donor-acceptor transitions in the form of a bulk heterojunction are a preferred embodiment of the invention.

The invention further provides an electroluminescent (EL) arrangement comprising an upper electrode, a lower electrode, wherein at least one of said electrodes is transparent, an electroluminescent layer and optionally an auxiliary layer, wherein the electroluminescent arrangement comprises at least one compound of the formula I as defined above. An EL arrangement is characterized by the fact that it emits light when an electrical voltage is applied with flow of current.

Such arrangements have been known for a long time in industry and technology as light-emitting diodes (LEDs). Light is emitted on account of the fact that positive charges (holes) and negative charges (electrons) combine with the emission of light. In the sense of this application the terms electroluminescing arrangement and organic light-emitting diode (OLEDs) are used synonymously. As a rule, EL arrangements are constructed from several layers. At least on of those layers contains one or more organic charge transport compounds. The layer structure is in principle as follows:
1. Carrier, substrate
2. Base electrode (anode)
3. Hole-injecting layer
4. Hole-transporting layer
5. Light-emitting layer
6. Electron-transporting layer
7. Electron-injecting layer
8. Top electrode (cathode)
9. Contacts
10. Covering, encapsulation.

This structure represents the most general case and can be simplified by omitting individual layers, so that one layer performs several tasks. In the simplest case an EL arrangement consists of two electrodes between which an organic layer is arranged, which fulfils all functions, including emission of light. The structure of organic light-emitting diodes and processes for their production are known in principle to those skilled in the art, for example from WO 2005/019373. Suitable materials for the individual layers of OLEDs are disclosed, for example, in WO 00/70655. Reference is made here to the disclosure of these documents. In principle OLEDs according to the invention can be produced by methods known to those skilled in the art. In a first embodiment, an OLED is produced by successive vapor deposition of the individual layers onto a suitable substrate. For vapor deposition, it is possible to use customary techniques such as thermal evaporation, chemical vapor deposition and others. In an alternative embodiment, the organic layers may be coated from solutions or dispersions in suitable solvents, for which coating techniques known to those skilled in the art are employed.

The invention is illustrated in detail with reference to the following nonrestrictive examples.

EXAMPLES

Abbreviations bipy 2,2'-bipyridine
COD 1,5-cyclooctadiene
DMF N,N-dimethylformamide
KOAc potassium acetate
MeOH methanol
NaOMe sodium methanolate
NBS N-bromosuccinimide
NIS N-iodosuccinimide
Pd(dppf)Cl$_2$ [1,1'-bis(diphenylphosphino)-ferrocene]dichloropalladium(II).dichloromethane I) Preparation of Compounds (I)

General Procedure

Field desorption mass spectra were obtained on a VG Instruments ZAB 2-SE-FPD spectrometer, with data collected between m/z 110-3,300. MALDI-TOF spectrometry was conducted on a Bruker Reflex IITOF spectrometer, utilizing a 337 nm nitrogen laser. Size-exclusion chromatography (SEC) analysis was performed with SDV (PSS) columns (106, 104, and 500 Å porosity) connected to RI and UV (254 nm) detectors against polystyrene standards, and calibrated for 1,4-poly(paraphenylene) (PPP) with THF as an eluting solvent. The high resolution mass spectrometry was performed on an ESI-Q-TOF system (maXis, BrukerDaltonics, Germany). The instrument was operated in wide pass quadrupole mode, for MS experiments, with the TOF data being collected between m/z 100-5,000. NMR measurements were recorded on a Bruker AVANCE 250 and a Bruker AVANCE 300 system. For a $^1$H NMR spectrum (5 mm BBI z-gradient probe) 128 transients were used with an 9.3 μs long 90° pulse and a 12600 Hz spectral width together with a recycling delay of 5 s. The temperature was kept at 298.3 K and regulated by a standard $^1$H methanol NMR sample using the topspin 3.0 software (Bruker). The proton and carbon spectra were measured in CD$_2$Cl$_2$ and CDCl$_3$ and the spectra were referenced as follows: for the residual CHDCl$_2$ at δ($^1$H)=5.32 ppm, CHCl$_3$ at δ($^1$H)=3.26 ppm. The assignment was accomplished by $^1$H,$^1$H COSY (correlated spectroscopy) 2D method. The spectroscopic widths of the homo-nuclear 2D COSY experiments were typically 14000 Hz in both dimension (f1 and f2) and the relaxation delay 1.2 s.

4,4,8,8,12,12-Hexamethyl-8,12-dihydro-4H-benzo[1,9]quinolizino[3,4,5,6,7-defg]-acridine was synthesized according to the literature:
(1) Fang, Z.; Zhang, X. H.; Lai, Y. H.; Liu, B. Chem. Commun. 2009, 920.
(2) Fang, Z.; Teo, T. L.; Cai, L. P.; Lai, Y. H.; Samoc, A.; Samoc, M. Org. Lett. 2009, 11, 1.
(3) Fang, Z.; Chellappan, V.; Webster, R. D.; Ke, L.; Zhang, T. F.; Liu, B.; Lai, Y. H. J. Mater. Chem. 2012, 22, 15397.

Example 1

2,6-Dibromo-4,4,8,8,12,12-hexamethyl-8,12-dihydro-4H-benzo[1,9]quinolizino[3,4,5,6,7-defg]acridine

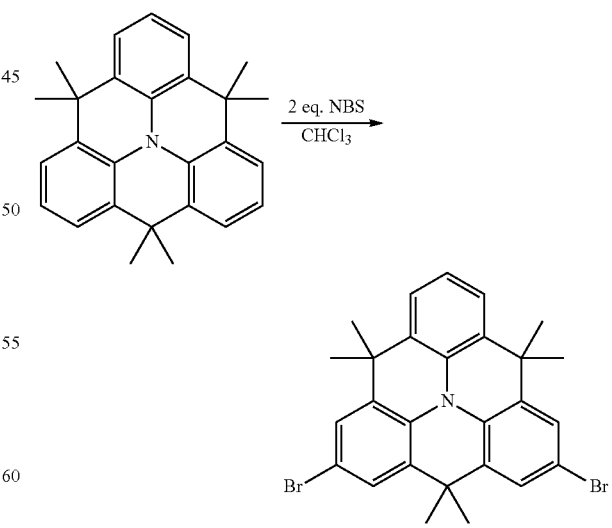

To a solution of 4,4,8,8,12,12-hexamethyl-8,12-dihydro-4H-benzo[1,9]quinolizino[3,4,5,6,7-defg]acridine (0.5 g, 1.37 mmol) in CHCl$_3$ (40 mL) at 0° C. was added N-bromosuccinimide (0.487 g, 2.74 mmol) over a period of 20 min.

While warming up to room temperature, the resulting solution was stirred in the absence of light overnight. The reaction was quenched with a saturated aqueous solution of $Na_2S_2O_3$. The resulting mixture was extracted with $CH_2Cl_2$ (3×) and the combined organic fractions were dried with $MgSO_4$. After filtration and evaporation of the solvent, the residue was subjected to column chromatography (silica, n-hexane/$CH_2Cl_2$ 4:1). Final recrystallization from ethanol yielded 2,6-Dibromo-4,4,8,8,12,12-hexamethyl-8,12-dihydro-4H-benzo[1,9]quinolizino[3,4,5,6,7-defg]acridine as a white powder (0.55 g, 77%).

$^1$H NMR ($CDCl_3$, 250 MHz, δ): 1.51 (s, 6H), 1.53 (s, 12H), 7.08 (t, $J_1=J_2=6.3$ Hz, 1H), 7.29 (d, J=7.5 Hz, 4H), 7.37 (dd, $J_1=J_2=2.5$ Hz, 4H). $^{13}$C NMR ($CDCl_3$, 63 MHz, δ): 132.2, 131.6, 131.5, 131.2, 131.0, 129.4, 126.5, 126.1, 123.7, 123.5, 115.8, 35.6, 33.0, 32.5, 29.7. FD-MS (8 kV): m/z=521.9 (100%, M$^+$). ESI-HR MS calcd for $C_{27}H_{25}Br_2N$ ([M+H]$^+$) 522.0432. found 522.0441.

Example 2

2,6-Dimethoxy-4,4,8,8,12,12-hexamethyl-8,12-dihydro-4H-benzo[1,9]quinolizino[3,4,5,6,7-defg]acridine This example demonstrates a possibility for the functionalization of the compounds (I).

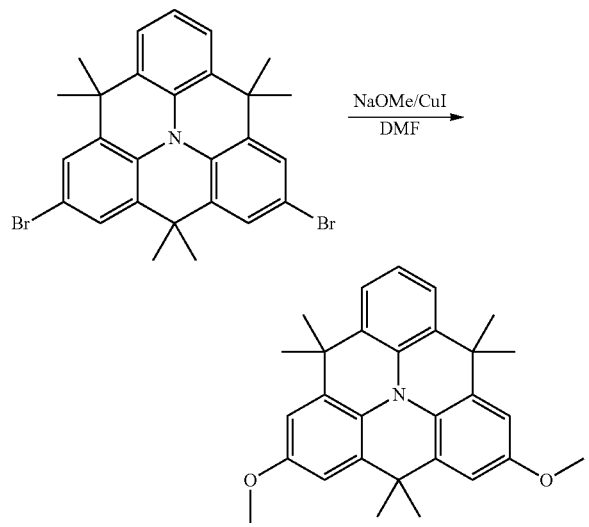

A flame-dried 50 mL Schlenk flask was equipped with sodium methanolate (1.90 g, 35.1 mmol, 6.5 mL; 5.4 M in MeOH), copper(I) iodide (0.77 g, 4.05 mmol) and 2,6-dibromo-4,4,8,8,12,12-hexamethyl-8,12-dihydro-4H-benzo[1,9]quinolizino[3,4,5,6,7-defg]acridine (0.21 g, 0.40 mmol), suspended in N,N-dimethylformamide (12.4 mL) and degassed with argon for 30 min. This mixture was stirred under an atmosphere of argon at 100° C. overnight. The reaction was stopped by addition of aqueous $NH_4Cl$ solution and the resulting mixture was extracted with $CH_2Cl_2$ (3×). The combined organic fractions were dried with $MgSO_4$, filtered and the solvents were evaporated. The crude product was purified by column chromatography (silica, n-hexane/EtOAc 8:1) yielding 2,6-dimethoxy-4,4,8,8,12,12-hexamethyl-8,12-dihydro-4H-benzo[1,9]quinolizino[3,4,5,6,7-defg]acridine as a greenish oil (0.12 g, 70%).

$^1$H NMR ($CD_2Cl_2$, 250 MHz, δ): 1.49 (s, 12H), 1.52 (s, 6H), 3.74 (broad s, 6H), 6.84 (s, 4H), 7.24 (m, 3H). $^{13}$C NMR ($CD_2Cl_2$, 63 MHz, δ): 30.1, 32.2, 55.8, 109.5, 110.5, 116.5, 123.0, 123.7, 123.9, 139.1 (10 out of 11). FD-MS (8 kV): m/z=425.7 (100%, M$^+$).

Example 3

2,6,10-Tribromo-4,4,8,8,12,12-hexamethyl-8,12-dihydro-4H-benzo[1,9]quinolizino[3,4,5,6,7-defg]acridine

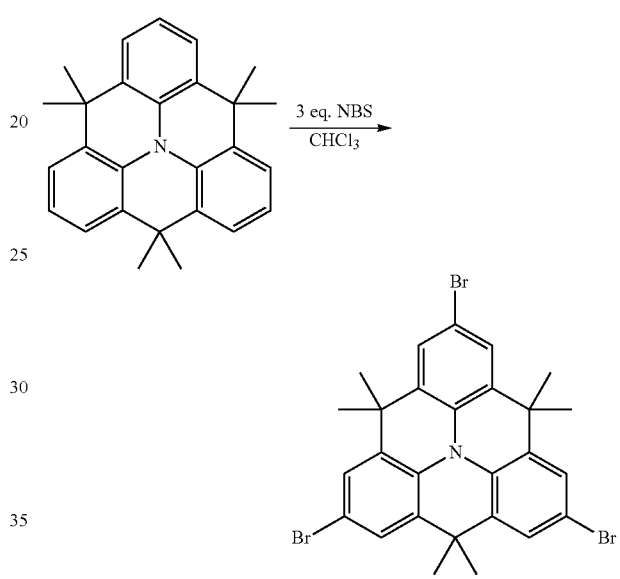

To a solution of 4,4,8,8,12,12-hexamethyl-8,12-dihydro-4H-benzo[1,9]quinolizino[3,4,5,6,7-defg]acridine (0.516 g, 1.41 mmol) in $CHCl_3$ (30 mL) at 0° C. was added N-bromosuccinimide (0.754 g, 4.24 mmol). While warming up to room temperature, the resulting solution was stirred in the absence of light overnight. The reaction was quenched with a saturated aqueous solution of $Na_2S_2O_3$. The resulting mixture was extracted with $CH_2Cl_2$ (3×) and the combined organic fractions were dried with $MgSO_4$. After filtration and evaporation of the solvent, the residue was subjected to column chromatography (silica, n-hexane/$CH_2Cl_2$ 4:1). Final recrystallization from ethanol yielded 2,6,10-tribromo-4,4,8,8,12,12-hexamethyl-8,12-dihydro-4H-benzo[1,9]quinolizino-[3,4,5,6,7-defg]acridine as a white powder (0.760 g, 90%).

$^1$H NMR ($CDCl_3$, 250 MHz, δ): 1.61 (s, 18H), 7.47 (s, 6H). $^{13}$C NMR ($CDCl_3$, 63 MHz, δ): 29.7, 32.5, 115.8, 123.6, 126.5, 131.8. FD-MS (8 kV): m/z=600.5 (100%, M$^+$).

Example 4

2,6,10-Trimethoxy-4,4,8,8,12,12-hexamethyl-8,12-dihydro-4H-benzo[1,9]quinolizino[3,4,5,6,7-defg]acridine This example demonstrates a possibility for the functionalization of the compounds (I).

45

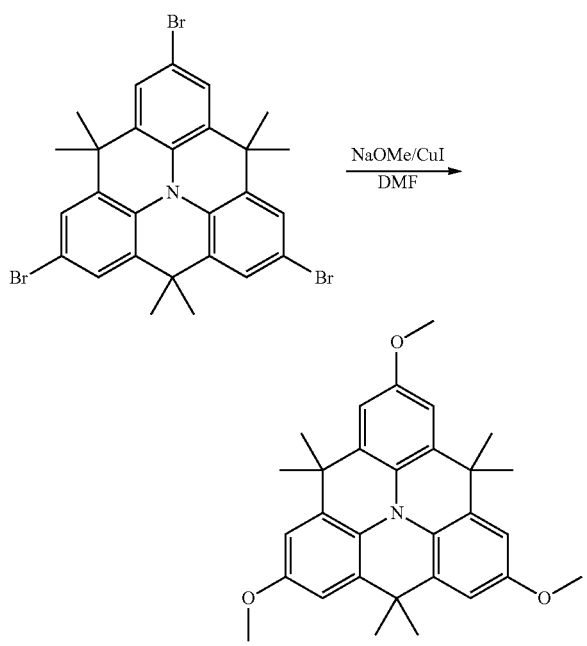

A flame-dried 50 mL Schlenk flask was equipped with sodium methanolate (5.24 g, 96.9 mmol, 17.9 mL; 5.4 M in MeOH), copper(I) iodide (0.683 g, 3.59 mmol) and 2,6,10-tribromo-4,4,8,8,12,12-hexamethyl-8,12-dihydro-4H-benzo[1,9]quinolizino[3,4,5,6,7-defg]acridine (0.216 g, 0.36 mmol), suspended in N,N-dimethylformamide (11 mL) and degassed with argon for 30 min. This mixture was stirred under an atmosphere of argon at 100° C. overnight. The reaction was stopped by addition of aqueous NH₄Cl solution and the resulting mixture was extracted with CH₂Cl₂ (3×). The combined organic fractions were dried with MgSO₄, filtered and the solvents were evaporated. The crude product was purified by column chromatography (silica, n-hexane/EtOAc 8:1) yielding 2,6,10-trimethoxy-4,4,8,8,12,12-hexamethyl-8,12-dihydro-4H-benzo[1,9]quinolizino-[3,4,5,6,7-defg]acridine as a white, crystalline solid (0.147 g, 88%).

$^1$H NMR (CD$_2$Cl$_2$, 250 MHz, δ): 1.52 (s, 18H), 3.79 (broad s, 9H), 6.85 (s, 6H). $^{13}$C NMR (CD$_2$Cl$_2$, 63 MHz, δ): 27.1, 30.1, 55.8, 92.5, 103.2, 107.8, (6 out of 7). FD-MS (8 kV): m/z=455.7 (100%, M⁺).

Example 5

2-Bromo-4,4,8,8,12,12-hexamethyl-8,12-dihydro-4H-benzo[1,9]quinolizino[3,4,5,6,7-defg]acridine

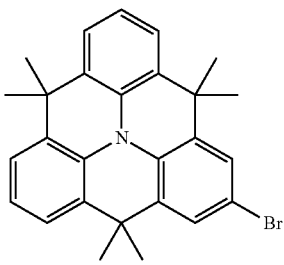 [SMILES: CC1(C)c2cccc3c2N2c4c1cccc4C(C)(C)c1cc(Br)cc(c12)C3(C)C]

46

To a solution of 4,4,8,8,12,12-hexamethyl-8,12-dihydro-4H-benzo[1,9]quinolizino[3,4,5,6,7-defg]acridine (5 g, 13.68 mmol) in CHCl₃ (133 mL) at 0° C. was added N-bromosuccinimide (2.44 g, 13.68 mmol) over a period of 20 min. While warming up to room temperature, the resulting solution was stirred in the absence of light overnight. The reaction was quenched with a saturated aqueous solution of Na₂S₂O₃. The resulting mixture was extracted with CH₂Cl₂ (3×) and the combined organic fractions were dried with MgSO₄. After filtration and evaporation of the solvent, the residue was subjected to column chromatography (silica, n-hexane/CH₂Cl₂ 4:1). Final recrystallization from ethanol yielded 2-bromo-4,4,8,8,12,12-hexamethyl-8,12-dihydro-4H-benzo[1,9]quinolizino[3,4,5,6,7-defg]acridine as a white powder (5.6 g, 92%).

$^1$H NMR (CD$_2$Cl$_2$, 250 MHz, δ): 1.63 (s, 12H), 1.66 (s, 6H), 7.18 (t, J$_1$=J$_2$=7.5 Hz, 2H), 7.43 (m, 4H), 7.51 (s, 2H). $^{13}$C NMR (CD$_2$Cl$_2$, 63 MHz, δ): 32.0, 131.5, 129.9, 129.3, 126.5, 126.1, 123.7, 123.3, 123.1, 115.5, 35.6, 35.4, 33.2, 32.8. FD-MS (8 kV): m/z=442.8 (100%, M⁺). ESI-HR MS calcd for C$_{27}$H$_{26}$BrN ([M+H]⁺) 444.1327. found 444.1331.

Example 6

Triangulene Dimer

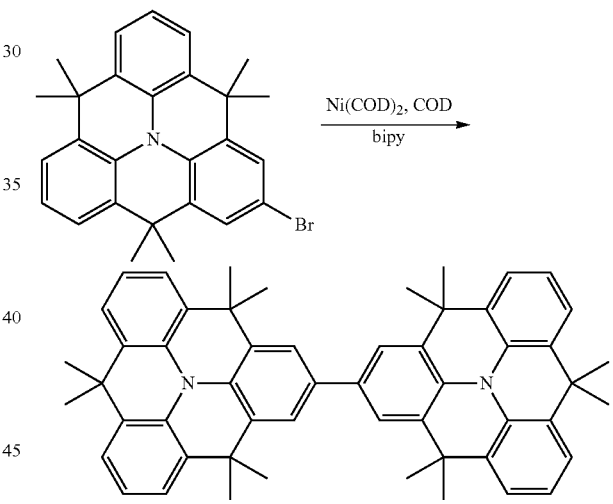

Bis(1,5-cyclooctadiene)nickel(0) (0.193 g, 0.70 mmol), 1,5-cyclooctadiene (0.08 g, 0.09 mL, 0.70 mmol) and 2,2'-bipyridine (0.109 g, 0.70 mmol) were added to a flame-dried 100 mL Schlenk flask, dissolved in 9.4 mL of anhydrous N,N-dimethylformamide and stirred for 30 min at 65° C. in the absence of light. A solution of 2-bromo-4,4,8,8,12,12-hexamethyl-8,12-dihydro-4H-benzo[1,9]quinolizino[3,4,5,6,7-defg]acridine (0.25 g, 0.56 mmol) in 18.8 mL of anhydrous toluene at 65° C. was added slowly via a double-tipped needle and the resulting mixture was stirred for two days at 85° C. The reaction was quenched by adding 10% aqueous hydrochloric acid, extracted three times with CH₂Cl₂ and the organic phase was dried with MgSO₄. After having removed the solvents in vacuo, the residue was subjected to column chromatography (silice, n-hexane/CH₂Cl₂ 3:1) leading to triangulene dimer as a white crystalline solid (0.165 g, 80%).

$^1$H NMR (CD$_2$Cl$_2$, 250 MHz, δ): 1.55 (s, 12H), 1.63 (s, 24H), 7.06 (t, J$_1$=J$_2$=5 Hz, 4H), 7.34 (pseudo t, J$_1$=J$_2$=5 Hz, 8H), 7.55 (s, 4H). $^{13}$C NMR (CDCl$_3$, 63 MHz, δ): 33.4, 36.0, 98.5, 115.5, 116.2, 122.1, 123.4, 123.9, 130.7 (9 out of 11). FD-MS (8 kV): m/z=728.1 (100%, M+), 364.5 (10%, M2+).

Example 7

4,4,8,8,12,12-Hexamethyl-2-(4,4,5,5-tetramethyl-1,3,2-dioxaborolan-2-yl)-8,12-dihydro-4H-benzo[1,9]quinolizino[3,4,5,6,7-defg]acridine

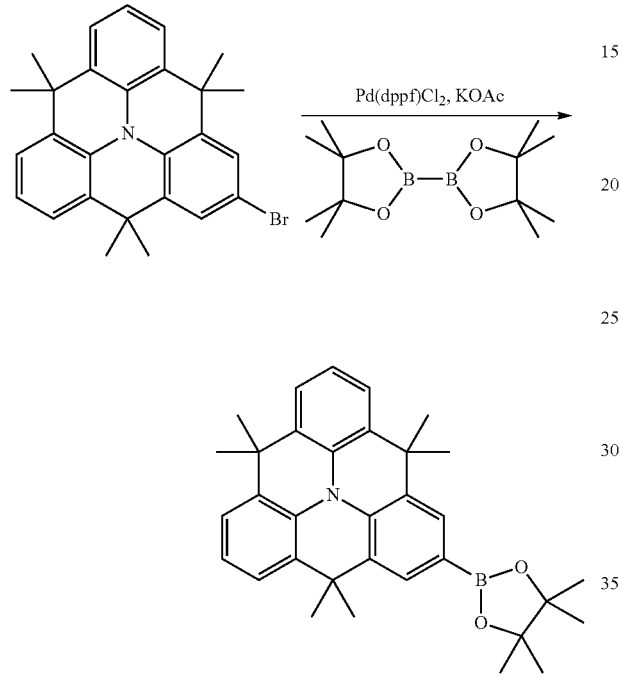

A flame-dried 250 mL Schlenk flask was equipped with 2-bromo-4,4,8,8,12,12-hexamethyl-8,12-dihydro-4H-benzo[1,9]quinolizino[3,4,5,6,7-defg]acridine (5.12 g, 11.52 mmol), bispinacolato diboron (3.66 g, 14.40 mmol) and potassium acetate (4.07 g, 41.47 mmol). The mixture was suspended in anhydrous N,N-dimethylformamide (96 mL) and degassed with argon for 1.5 hours. Subsequently, [1,1'-bis(diphenylphosphino)-ferrocene]dichloropalladium(II) .dichloromethane was added and the resulting mixture was stirred under an argon atmosphere for 15 hours at 85° C. The reaction was stopped by addition of water and the resulting mixture was extracted with $CH_2Cl_2$ (3×). The combined organic fractions were dried with $MgSO_4$, filtered and the solvents were evaporated. The crude product was purified by column chromatography (silica, n-hexane//$CH_2Cl_2$ 2:3) yielding 4,4,8,8,12,12-hexamethyl-2-(4,4,5,5-tetramethyl-1,3,2-dioxaborolan-2-yl)-8,12-dihydro-4H-benzo[1,9]quinolizino[3,4,5,6,7-defg]acridine as a colorless, crystalline solid (4.88 g, 86%).

$^1$H NMR (CDCl$_3$, 250 MHz, δ): 1.41 (s, 12H), 1.68 (s, 18H), 7.19 (t, $J_1$=$J_2$=8.75 Hz, 2H), 7.45 (d, J=7.5 Hz, 4H), 7.82 (s, 2H). $^{13}$C NMR (CDCl$_3$, 63 MHz, δ): 25.1, 33.2, 33.6, 35.8, 84.0, 123.6, 123.9, 124.1, 129.1, 130.3, 130.4, 130.8, 132.0, 134.9. ESI-HR MS calcd for $C_{33}H_{39}BNO_2$ ([M+H]$^+$) 492.3074. found 492.3004.

Example 8

2-Bromo-4,4,8,8,12,12-hexamethyl-6-(4,4,5,5-tetramethyl-1,3,2-dioxaborolan-2-yl)-8,12-dihydro-4H-benzo[1,9]quinolizino[3,4,5,6,7-defg]acridine

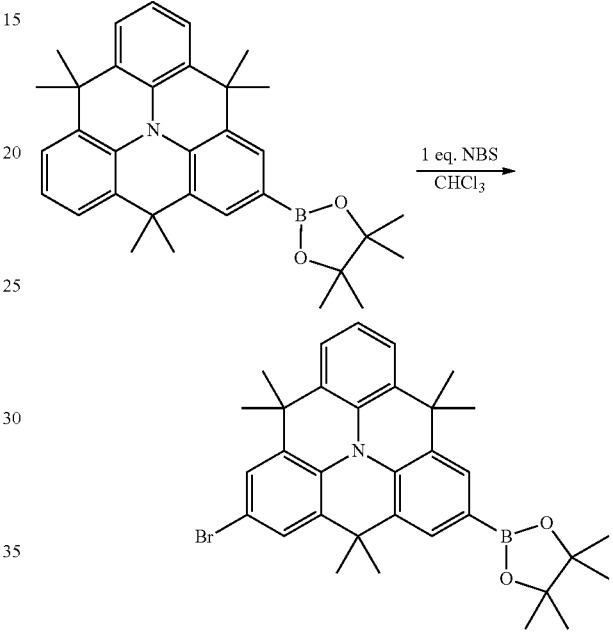

To a solution of 4,4,8,8,12,12-hexamethyl-2-(4,4,5,5-tetramethyl-1,3,2-dioxaborolan-2-yl)-8,12-dihydro-4H-benzo[1,9]quinolizino[3,4,5,6,7-defg]acridine (2.10 g, 4.27 mmol) in CHCl$_3$ (77 mL) at 0° C. was added N-bromosuccinimide (0.761 g, 4.27 mmol) over a period of 20 min. While warming up to room temperature, the resulting solution was stirred in the absence of light overnight. The reaction was quenched with a saturated aqueous solution of Na$_2$S$_2$O$_3$. The resulting mixture was extracted with CH$_2$Cl$_2$ (3×) and the combined organic fractions were dried with MgSO$_4$. After filtration and evaporation of the solvent, the residue was subjected to column chromatography (silica, n-hexane/CH$_2$Cl$_2$ 2:3). Final recrystallization from ethanol yielded 2-bromo-4,4,8,8,12,12-hexamethyl-6-(4,4,5,5-tetramethyl-1,3,2-dioxaborolan-2-yl)-8,12-dihydro-4H-benzo[1,9]quinolizino[3,4,5,6,7-defg]acridine as a white powder (1.87 g, 77%).

$^1$H NMR (CDCl$_3$, 250 MHz, δ): 1.40 (s, 12H), 1.65 (s, 12H), 1.67 (s, 6H), 7.20 (t, $J_1$=$J_2$=8.75 Hz, 2H), 7.44 (dd, $J_1$=8.75 Hz, $J_2$=1.5 Hz, 2H), 7.52 (s, 2H), 7.81 (d, J=7.5 Hz, 2H). $^{13}$C NMR (CDCl$_3$, 75 MHz, δ): 25.1, 32.8, 33.2, 33.3, 84.0, 123.9, 124.0, 124.2, 126.5, 126.7, 130.2, 130.6 (12 out of 17 expected). ESI-HR MS calcd for $C_{33}H_{37}BBrNO_2$ ([M+H]$^+$) 570.2179. found 570.2190.

Example 9

2,6-Diiodo-4,4,8,8,12,12-hexamethyl-8,12-dihydro-4H-benzo[1,9]quinolizino[3,4,5,6,7-defg]acridine

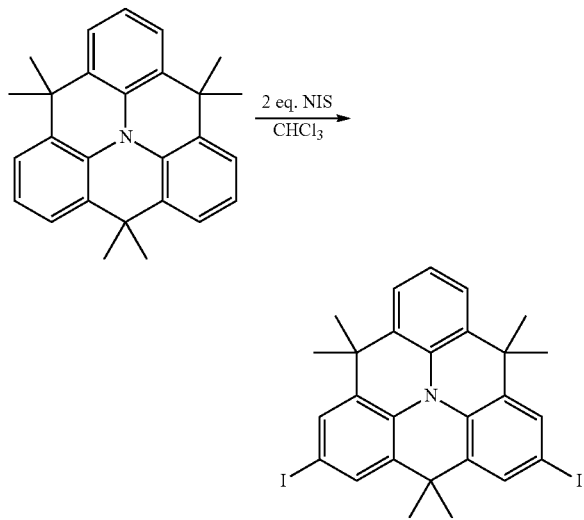

To a solution of 4,4,8,8,12,12-hexamethyl-8,12-dihydro-4H-benzo[1,9]quinolizino[3,4,5,6,7-defg]acridine (DTPA) (1.52 g, 4.17 mmol) in CHCl₃ (40 mL) at 0° C. was added N-iodosuccinimide (2.38 g, 10.58 mmol) over a period of 20 min (for completion of the reaction an excess of NIS was necessary). After slowly warming up to room temperature, the resulting solution was stirred at 50° C. in the absence of light for 96 hours. The reaction was quenched with a saturated aqueous solution of Na₂S₂O₃. The resulting mixture was extracted with CH₂Cl₂ (3×) and the combined organic fractions were dried with MgSO₄. After filtration and evaporation of the solvent, the residue was subjected to column chromatography (silica, n-hexane/CH₂Cl₂ 4:1). Final recrystallization from ethanol yielded 2,6-diiodo-4,4,8,8,12,12-hexamethyl-8,12-dihydro-4H-benzo[1,9]quinolizino[3,4,5,6,7-defg]acridine as a white powder (2.3 g, 89%).

$^1$H NMR (CD$_2$Cl$_2$, 250 MHz, δ): 1.55 (s, 6H), 1.58 (s, 12H), 7.15 (t, J$_1$=J$_2$=8.75 Hz, 1H), 7.39 (d, J=8.75 Hz, 2H), 7.63 (dd, J$_1$=5 Hz, J$_2$=2.5 Hz, 4H). $^{13}$C NMR (CD$_2$Cl$_2$, 63 MHz, δ): 132.2, 131.6, 131.5, 131.2, 131.0, 129.4, 126.5, 126.1, 123.7, 123.5, 115.8, 35.6, 33.0, 32.5, 29.7. ESI-HR MS calcd for C$_{27}$H$_{25}$I$_2$N ([M+H]$^+$) 618.0155. found 618.0161.

Example 10

Heterotriangulene Trimer

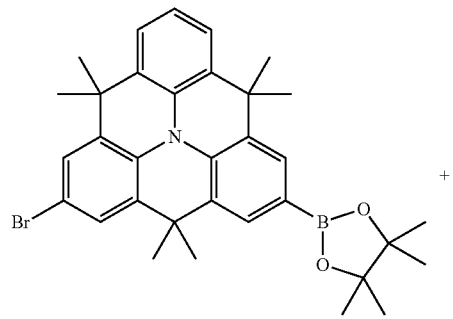

+

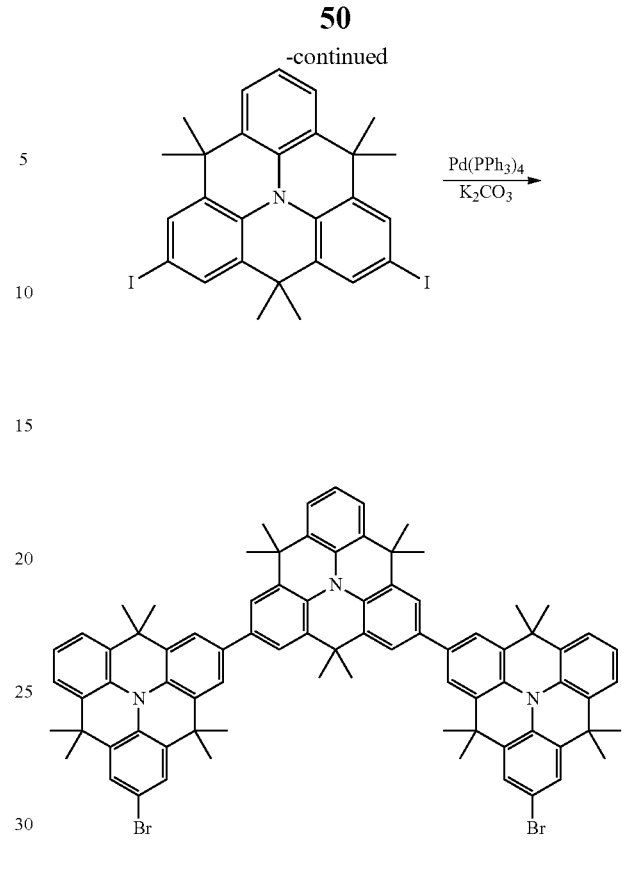

A 250 mL Schlenk tube was equipped with 2-bromo-4,4,8,8,12,12-hexamethyl-6-(4,4,5,5-tetramethyl-1,3,2-dioxaborolan-2-yl)-8,12-dihydro-4H-benzo[1,9]quinolizino[3,4,5,6,7-defg]acridine (0.750 g, 1.21 mmol) and 2,6-diiodo-4,4,8,8,12,12-hexamethyl-8,12-dihydro-4H-benzo[1,9]quinolizino[3,4,5,6,7-defg]acridine (1.42 g, 2.49 mmol) followed by three times evacuating and backfilling with argon. After the addition of 55 mL of toluene, 27.5 mL of an aqueous 2M Na₂CO₃ solution and three drops of aliquat 336 the resulting mixture was degassed with argon for one hour. To this mixture Pd(PPh₃)₄ (0.112 g, 4 mol %) was added and it was stirred under an atmosphere of argon at 65° C. for three days. Washing the aqueous phase three times with toluene, drying the combined organic phases with MgSO₄ and evaporating of the solvent in vacuo resulted in a crude mixture which was subjected to column chromatography (silica, n-hexane/CH₂Cl₂ 3:1). Heterotriangulene trimer was obtained as pale yellow solid (0.836 g, 55%).

$^1$H NMR (CD$_2$Cl$_2$, 250 MHz, δ): 1.54 (s, 12H), 1.65 (m, 36H), 1.73 (s, 6H), 7.09 (t, J$_1$=J$_2$=7.5 Hz, 3H), 7.37 (m, 10H), 7.57 (m, 8H). $^{13}$C NMR (CD$_2$Cl$_2$, 75 MHz, δ): 136.2, 132.6, 132.5, 131.1, 131.0, 130.3, 129.8, 126.6, 124.3, 123.9, 123.7, 122.5, 122.1, 115.9, 50.8, 36.2, 36.0, 33.6, 33.1, 33.0. FD-MS (8 kV): m/z=1250.4 (100%, M$^+$), 624.8 (85%, M$^{2+}$). MALDI-TOF MS (dithranol): m/z=1248.65 (100%) [M+H]$^+$ ESI-HR MS calcd for C$_{81}$H$_{75}$Br$_2$N$_3$ ([M+H]$^+$) 1248.4406. found 1248.4392.

Example 11

Heterotriangulene Nonamer

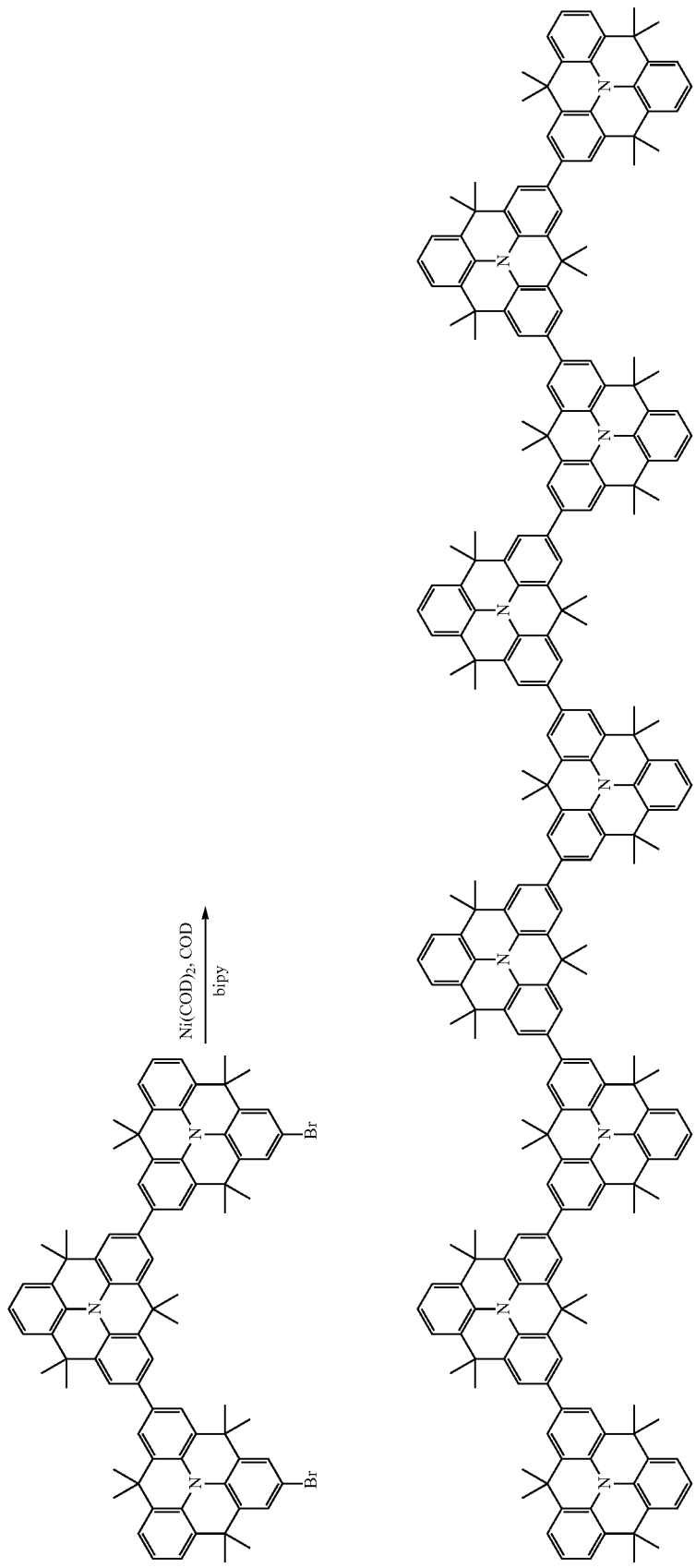

Bis(1,5-cycloocatdiene)nickel(0) (0.381 g, 1.39 mmol), 1,5-cyclooctadiene (0.150 g, 0.17 mL, 1.39 mmol) and 2,2'-bipyridine (0.216 g, 1.39 mmol) were added to a flame-dried 250 mL Schlenk flask, dissolved in 30 mL of anhydrous N,N-dimethylformamide and stirred for 30 min at 65° C. in the absence of light. A solution of dibromo-triangulene trimer (0.825 g, 0.66 mmol) in 141 mL of anhydrous toluene at 65° C. was added slowly via a double-tipped needle and the resulting mixture was stirred for two days at 85° C. The reaction was quenched by adding 10% aqueous hydrochloric acid, extracted three times with $CH_2Cl_2$ and the organic phase was dried with $MgSO_4$. After having removed the solvents in vacuo, the residue was filtrated over a plug of silica (n-hexane/$CH_2Cl_2$ 1:1). Finally, heterotriangulene nonamer was removed from the hexameric macrocycle with the help of preparative size exclusion chromatography (BioBeads S-X1, toluene) and obtained after precipitation into methanol as a yellow solid (0.108 g, 15%).

$^1$H NMR ($CD_2Cl_2$, 250 MHz, δ): 1.67 (s, 108H), 1.75 (s, 54H), 7.10 (broad m, 11H), 7.37 (br m, 18H), 7.59 (br m, 36H). FD-MS (8 kV): m/z=3273.7 (100%, M$^+$), 1636.8 (50%, M$^{2+}$). MALDI-TOF MS (dithranol): m/z=3270.01 (100%) [M+H]$^+$.

Example 12

Heterotriangulene Polymer

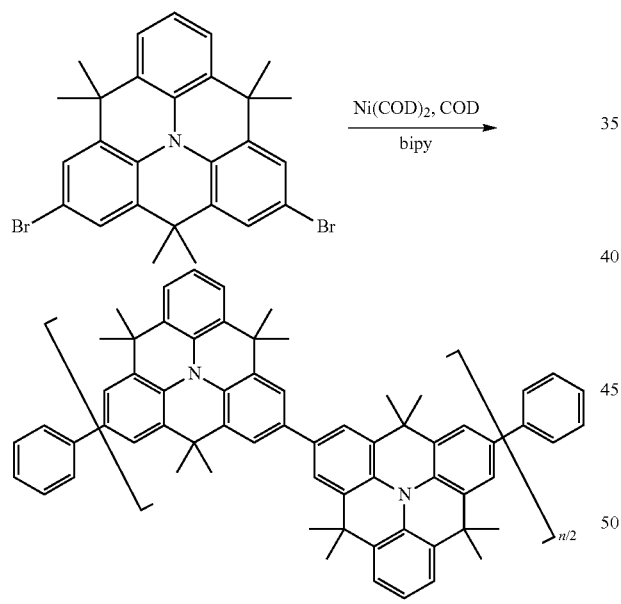

Bis(1,5-cycloocatdiene)nickel(0) (0.460 g, 1.67 mmol), 1,5-cyclooctadiene (0.181 g, 0.21 mL, 1.67 mmol) and 2,2'-bipyridine (0.261 g, 1.67 mmol) were added to a flame-dried 100 mL Schlenk flask, dissolved in 7 mL of anhydrous toluene and N,N-dimethylformamide (2:1) and stirred for 30 min at 65° C. in the absence of light. A solution of 2,6-dibromo-4,4,8,8,12,12-hexamethyl-8,12-dihydro-4H-benzo[1,9]quinolizino[3,4,5,6,7-defg]acridine (0.350 g, 0.67 mmol) in 23 mL of anhydrous toluene at 65° C. was added quickly via a double-tipped needle and the resulting mixture was stirred for two days at 85° C. in the absence of light. After addition of 1 mL of bromobenzene the mixture was stirred for additional two hours. Subsequently the reaction mixture was poured into 160 mL of MeOH/HCl (30:1) and was stirred for one hour and the precipitate was filtered. After repeated precipitation in MeOH/HCl, the polymer was subjected to soxhlet extraction using acetone and hexane. Final precipitation lead to a white solid (0.160 g, 66%). $^1$H NMR ($CD_2Cl_2$, 250 MHz, δ): 1.67 (br, 6H), 1.76 (br, 12H), 7.09 (br, 1H), 7.40 (br, 2H), 7.62 (br, 4H). SEC (THF, PS-standard): $M_n$=10,500 g/mol, $M_w$=17,800 g/mol, PDI=1.7, $DP_n$~29.

II) Preparation and Characterization of Dye-Sensitized and of Perovskite-Based Solar Cells Example 13

Preparation of Solid-State Dye-Sensitized Solar-Cells

A $TiO_2$ blocking layer was prepared on a fluorine-doped tin oxide (FTO)-covered glass substrate using spray pyrolysis (cf. B. Peng, G. Jungmann, C. Jager, D. Haarer, H. W. Schmidt, M. Thelakkat, Coord. Chem. Rev. 2004, 248, 1479). Next, a $TiO_2$ paste (Dyesol), diluted with terpineol, was applied by screen printing, resulting in a film thickness of 1.7 μm. All films were then sintered 45 min at 450° C., followed by treatment in a 40 mM aqueous solution of $TiCl_4$ at 60° C. for 30 min, followed by a further sintering step. The prepared samples with $TiO_2$ layers were pretreated with a 5 mM solution of the additive 2-(p-butoxyphenyl)acetohydroxamic acid sodium salt ("ADD1") in ethanol (this additive is described on page 52 of WO 2012/001628 A1 as "Example No. 6"). The electrodes were then dyed in 0.5 mM dye solution of the following dye in $CH_2Cl_2$:

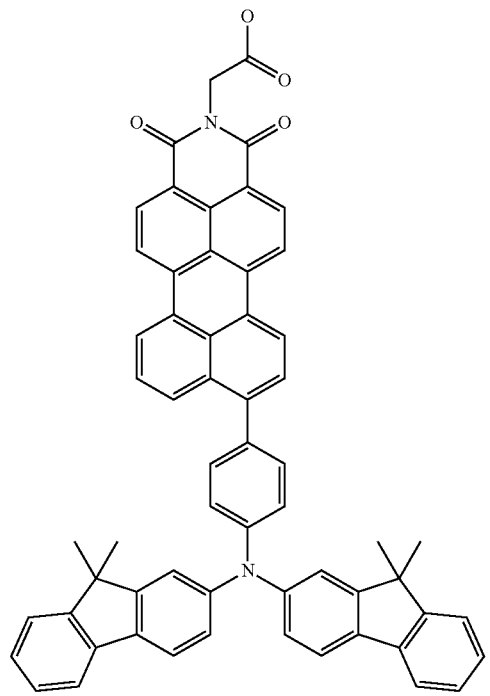 [SMILES: CC1(C)c2ccccc2-c2ccc(N(c3ccc(-c4ccc5c6ccc7c8c(ccc(c9cccc4c95)c86)C(=O)N(CC(=O)O)C7=O)cc3)c3ccc4c(c3)C(C)(C)c3ccccc3-4)cc21]

The hole transporting materials spiro-MeOTAD (comparison example; commercially available from Merck KGaA, Darmstadt as SHT-263 Livilux®) and the compounds of examples 11 (nonamer) was applied by spin-coating from a solution in dichloromethane (200 mg/mL) also containing 20 mM Li(CF$_3$SO$_2$)$_2$N. Fabrication of the device was completed by evaporation of 200 nm of silver as the counter electrode. The active area of the sDSSC was defined by the size of these contacts (0.13 cm$^2$), and the cells were masked by an aperture of the same area for measurements.

Example 14

Preparation of a TiO$_2$-Based Perovskite Cell Comprising (CH$_3$NH$_3$)PbI$_3$ as Absorber Material A TiO$_2$ blocking layer was prepared on a fluorine-doped tin oxide (FTO)-covered glass substrate using spray pyrolysis (cf. B. Peng, G. Jungmann, C. Jager, D. Haarer, H. W. Schmidt, M. Thelakkat, Coord. Chem. Rev. 2004, 248, 1479). Next, a TiO$_2$ paste (Dyesol), diluted with ethanol (1:3), was applied by spincoating, resulting in a film thickness of 500 nm. The films were then heated up to 450° C. in 45 min and sintered 30 min at 450° C. A solution of 196 mg CH$_3$NH$_3$I, 573 mg PbI$_2$ and 1 mL γ-butyrolactone was stirred 1 hour at 60° C. and filtered afterwards through a 2 µl syringe. The sintered substrates were placed on a hotplate at 100° C., and after a short cool down 100 µL of the Perovskite-solution were applied to the whole substrate with an Eppendorf pipette and spinned off after 20 sec at 2000 rpm for 45 seconds. The coated substrate was kept on the hotplate at 50° C. for further 5 seconds. After letting the coated substrates cool down to ambient temperature (10 minutes), 125 µL of a solution of spiro-MeOTAD (80 mM), solid LiTFSI (12 mM) and 73 µm 4-t-butylpyridine were applied by spin-coating from a solution in dichloromethane (200 mg/mL). Fabrication of the device was completed by evaporation of 200 nm of silver as the counter electrode.

Example 15

Preparation of an Al$_2$O$_3$-Based Perovskite Cell Comprising (CH$_3$NH$_3$)PbI$_2$Cl as Absorber Material A TiO$_2$ blocking layer was prepared on a fluorine-doped tin oxide (FTO)-covered glass substrate using spray pyrolysis (cf. B. Peng, G. Jungmann, C. Jager, D. Haarer, H. W. Schmidt, M. Thelakkat, Coord. Chem. Rev. 2004, 248, 1479). Next, Al$_2$O$_3$ diluted with ethanol (1.1:1), was applied by spincoating, resulting in a film thickness of 350 nm. The films were then heated up to 500° C. in 45 min and sintered 30 min at 500° C. A solution in dimethylformamide containing 270 mg/ml CH$_3$NH$_3$I and 158 mg/ml PbCl$_2$ was stirred 1 hour at 60° C. and filtered afterwards through a 2 µl syringe. The sintered substrates were placed on a hotplate at 100° C. and after a short cool down 100 µL of the Perovskite-Solution was applied to the whole substrate with an Eppendorf pipette and spinned off after 20 sec at 2000 rpm for 45 seconds. The coated substrate was kept on the hotplate at 100° C. for further 45 minutes. After letting the coated substrates cool down to ambient temperature (10 minutes), 125 µL of a solution of spiro-MeOTAD (80 mM), solid LiTFSI (12 mM) and 73 µm 4-t-butylpyridine were applied by spin-coating from a solution in dichloromethane (200 mg/mL). Fabrication of the device was completed by evaporation of 200 nm of silver as the counter electrode.

Application Properties

Example 16

The current-voltage characteristics for all cells were measured with a Keithley 2400 under 1000 W/m$^2$, AM 1.5 G conditions (LOT ORIEL 450 W). The incident photon to current conversion efficiencies (IPCE) were obtained with an Acton Research Monochromator using additional white background light illumination.

The samples were illuminated with monochromatic light from the quartz monochromator with deuterium lamp. The power of the incident light beam was (2-5)·10$^{-8}$ W. The negative voltage of −300 V was supplied to the sample substrate. The counter-electrode with the 4.5×15 mm$^2$ slit for illumination was placed at 8 mm distance from the sample surface. The counter-electrode was connected to the input of the BK2-16 type electrometer, working in the open input regime, for the photocurrent measurement. A strong photocurrent was flowing in the circuit under illumination. The photocurrent J is strongly dependent on the incident light photon energy hv. The $J^{0.5}$=f(hv) dependence was plotted. Usually the dependence of the photocurrent on incident light quanta energy is well described by linear relationship between $J^{0.5}$ and hv near the threshold (cf. E. Miyamoto, Y. Yamaguchi, M. Yokoyama, Electrophotography 1989, 28, 364 and M. Cordona, L. Ley, Top. Appl. Phys. 1978, 26, 1). The linear part of this dependency was extrapolated to the hv axis and $J_p$ value was determined as the photon energy at the interception point. Table 1 shows the results for the three different cell types from examples 13-15.

TABLE 1

| cell from example no. | Isc [mA/cm$^2$] | Voc [mV] | FF [%] | ETA [%] |
|---|---|---|---|---|
| 13 (sDSSC) | 5.35 | 900 | 58 | 2.8 |
| 14 (TiO$_2$-based Perovskite) | 10.52 | 900 | 55 | 5.2 |
| 15 (Al$_2$O$_3$-based Perovskite) | 7.08 | 1100 | 50 | 3.9 |

This demonstrates that the new hole conducting materials according to the invention are versatile in their use and generally show good application properties in the different cell types.

Example 17

Thermal Stability

Lifetime test of the DSSC of example 13 comprising the triangulene nonamer of example 11 as hole transport material (HTM) and the DSSC comprising spiro-MeOTAD as HTM as comparative example. The DSSCs were sealed and constantly kept at 30% humidity after fabrication. The initial values were measured at 25° C. The temperature was then raised to 60° C. and kept constant until a lifetime of 312 hours was reached. The results of the DSSC according to the invention comprising the triangulene nonamer are shown in table 2. The results of the comparative DSSC comprising spiro-MeOTAD as HTM are shown in table 3. FIG. 1 shows a direct comparison of the efficiency (i) over the lifetime of a DSSC of both cells.

TABLE 2

| (DSSC comprising the triangulene nonamer as HTM) | | | | | |
|---|---|---|---|---|---|
| temperature [° C.] | hours | Isc [mA/cm$^2$] | Voc [mV] | FF [%] | ETA [%] |
| 25° C. | 0 | 5.35 | 900 | 58 | 2.8 |
| 60° C. | 48 | 4.53 | 920 | 59 | 2.5 |
| 60° C. | 120 | 5.76 | 900 | 50 | 2.6 |

TABLE 2-continued (DSSC comprising the triangulene nonamer as HTM)

| temperature [°C.] | hours | Isc [mA/cm$^2$] | Voc [mV] | FF [%] | ETA [%] |
|---|---|---|---|---|---|
| 60° C. | 216 | 5.78 | 900 | 49 | 2.5 |
| 60° C. | 312 | 5.45 | 900 | 50 | 2.5 |

($V_{OC}$: Open circuit voltage; $I_{SC}$: Short circuit current; FF: Fill Factor; η: Efficiency)

TABLE 3

(DSSC comprising spiro-MeOTAD as HTM)

| temperature [°C.] | hours | Isc [mA/cm$^2$] | Voc [mV] | FF [%] | ETA [%] |
|---|---|---|---|---|---|
| 25° C. | 0 | 8.7 | 860 | 69 | 5.1 |
| 60° C. | 120 | 6.98 | 840 | 44 | 2.6 |
| 60° C. | 144 | 4.66 | 840 | 52 | 2.0 |
| 60° C. | 168 | 5.57 | 840 | 46 | 2.1 |
| 60° C. | 192 | 4.14 | 840 | 53 | 1.9 |
| 60° C. | 264 | 3.99 | 840 | 54 | 1.8 |
| 60° C. | 288 | 3.76 | 820 | 57 | 1.7 |
| 60° C. | 312 | 3.74 | 840 | 54 | 1.7 |

As can be seen, the DSSC comprising spiro-MeOTAD loses a considerable amount of efficiency during heat treatment, whereas the DSSC comprising the triangulene nonamer of example 11 is in the same region of the initial measurement.

Example 18

UV Stability of the Perovskite Al$_2$O$_3$ Cell

Table 4 shows the UV stability of the cell of example 15 comprising a Perovskite absorber and the triangulene nonamer of example 11 as hole transport material (HTM). The following values were taken:

1) before UV
2) after 20 min UV
3) after one night recovering and another 20 min UV
4) after one night recovering and another 90 min UV

TABLE 3

| | ETA [%] |
|---|---|
| before UV (1) | 3.8 |
| after UV 1 (2) | 3.9 |
| after UV 2 (3) | 3.8 |
| after UV 3 (4) | 3.7 |

The invention claimed is:

1. A compound of the general formula 1:

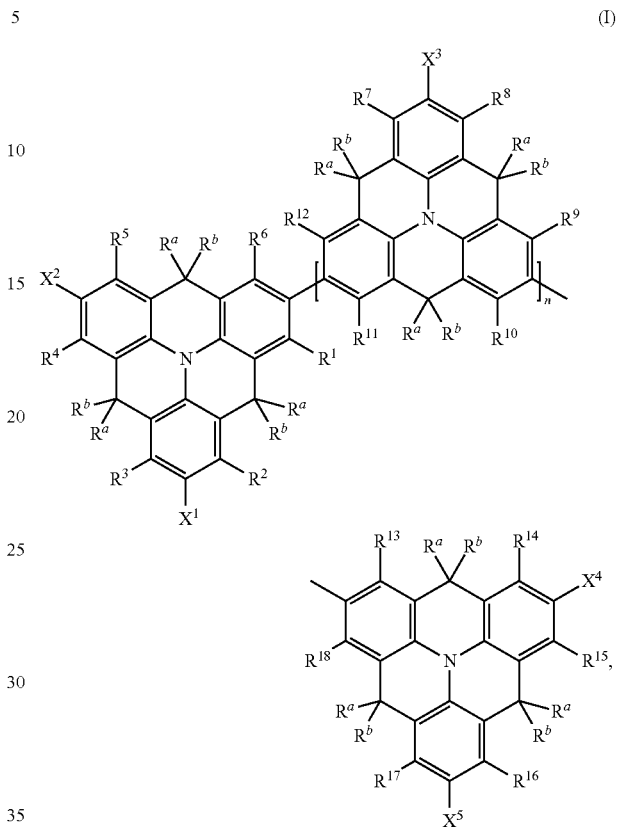

wherein n is 1 to 100, $X^1$, $X^2$, $X^3$, $X^4$, and $X^5$ are independently of one another selected from hydrogen, F, Cl, Br, I, CN, B(OR$^c$)$_2$, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, NE$^1$ E$^2$, where E$^1$ and E$^2$ are each independently selected from hydrogen, alkyl, cycloalkyl, heterocycloalkyl, aryl or hetaryl, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl) amino, aryl, aryloxy, arylthio, (monoaryl)amino, (diaryl)amino, hetaryl, hetaryloxy, hetarylthio, (monohetaryl)amino and (dihetaryl)amino, wherein R$^c$ is selected from in each case unsubstituted or substituted alkyl, cycloalkyl or aryl, or wherein two radicals R$^c$ may together form a divalent bridging group selected from in each case unsubstituted or substituted C$_2$-C$_{10}$-alkylene, C$_3$-C$_6$-cycloalkylene and C$_6$-C$_{14}$-arylene, wherein C$_2$-C$_{10}$-alkylene, C$_3$-C$_6$-cycloalkylene and C$_6$-C$_{14}$-arylene may carry one or more identical or different C$_1$-C$_{12}$-alkyl radicals, $R^a$ and $R^b$ are independently of one another selected from hydrogen and unsubstituted $C_1$-$C_6$-alkyl, $R^1, R^2, R^3, R^4, R^5, R^6, R^{13}, R^{14}, R^{15}, R^{16}, R^{17}, R^{18}, R^7, R^8, R^9, R^{10}, R^{11}$ and $R^{12}$ are independently of one another selected from hydrogen, and in each case unsubstituted or substituted alkyl, alkoxy, alkenyl, alkadienyl, alkynyl, cycloalkyl, cycloalkoxy, bicycloalkyl, cycloalkenyl, heterocycloalkyl, heterocycloalkyloxy, aryl, aryloxy, heteroaryl and heteroaryloxy;

and wherein said compound of the general formula (1) has a linear structure.

2. A compound according to claim 1, wherein n is 1 to 50.

3. A compound according to claim 1, wherein n is 5, 6, 7, 8 or 9.

4. A compound according to claim 1, wherein n is in a range of from 16 to 100.

5. A compound according to claim 1, wherein the radicals $R^a$ and $R^b$ are all methyl.

6. A compound according to claim 1, wherein the radicals $R^1, R^2, R^3, R^4, R^5, R^6, R^{13}, R^{14}, R^{15}, R^{16}, R^{17}, R^{18}$ and, if present, $R^7, R^8, R^9, R^{10}, R^{11}$ and $R^{12}$ are all hydrogen.

7. A compound according to claim 1, wherein the radicals $X^3$ are all hydrogen.

8. A compound according to claim 1, wherein one of the radicals $X^1$ and $X^2$ is hydrogen and the other is selected from the group consisting of hydrogen and unsubstituted or substituted alkyl, alkoxy, alkylthio, cycloalkyl, aryl, aryloxy and arylthio.

9. A compound according to claim 1, wherein one of the radicals $X^4$ and $X^5$ is hydrogen and the other is selected from the group consisting of hydrogen and unsubstituted or substituted alkyl, alkyl, alkoxy, alkylthio, cycloalkyl, aryl, aryloxy and arylthio.

10. A compound according to claim 1, wherein the radicals $X^1, X^2, X^4$, and $X^5$ are all hydrogen.

11. A compound of the formula (I.a):

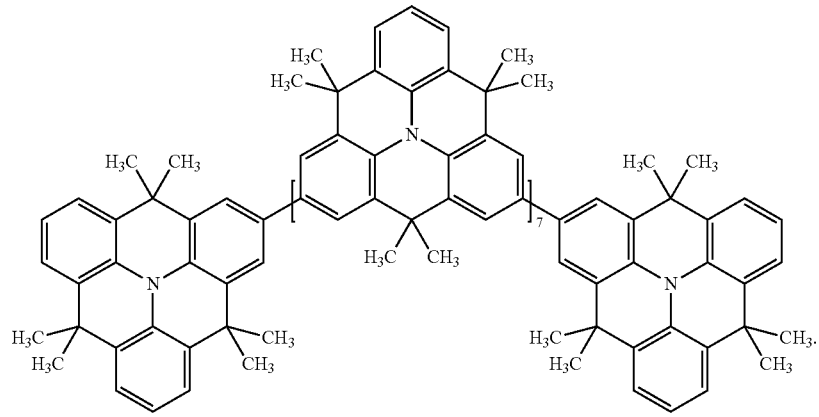

(I.a)

12. A compound of the formula (I.b):

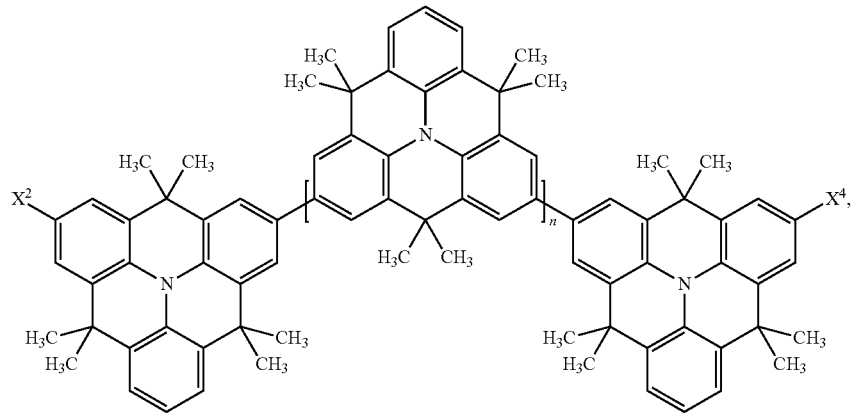

(I.b)

wherein
n is 16 to 100,
X² and X⁴ are independently of one another selected from the group consisting of hydrogen, and in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyDamino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino.

13. A composition comprising at least one compound of general formula (I) as defined in claim 1.

14. A process for the preparation of a compound of the formula I,

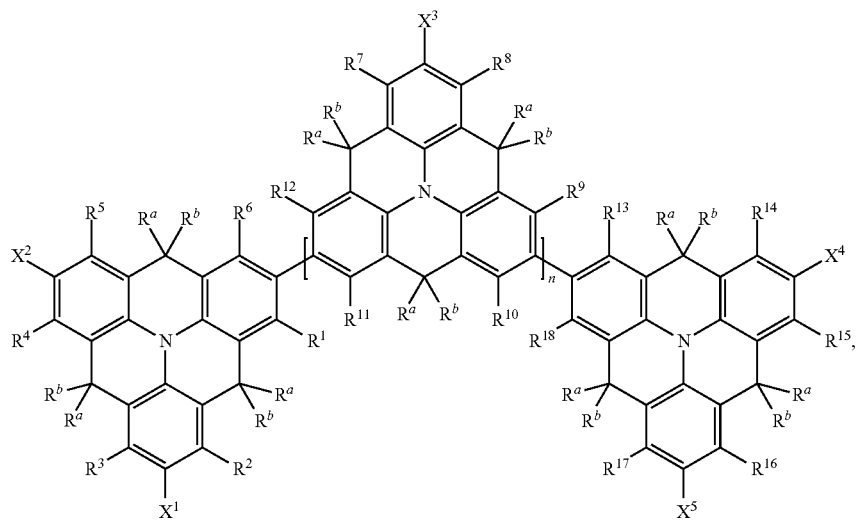

wherein
is 1 to 100,
X¹, X², X³, X⁴, and X⁵ are independently of one another selected from the group consisting of hydrogen, F, Cl, Br, I, CN, B(OR$^c$)₂,
hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, NE¹E², where E¹ and E² are each independently selected from hydrogen, alkyl, cycloalkyl, heterocycloalkyl, aryl or hetaryl,
in each case unsubstituted or substituted alkyl, alkoxy, alkylthio, (monoalkyl)amino, (dialkyl)amino, cycloalkyl, cycloalkoxy, cycloalkylthio, (monocloalkyl)amino, (dicloalkyl)amino, heterocloalkyl, heterocycloalkoxy, heterocycloalkylthio, (monoheterocycloalkyl)amino, (diheterocycloalkyDamino, aryl, aryloxy, arylthio, (monoaryl)amino, (diaryl)amino, hetaryl, hetaryloxy, hetarylthio, (monohetaryl)amino and (dihetaryl)amino,
wherein R$^c$ is selected from in each case unsubstituted or substituted alkyl, cycloalkyl or aryl, or wherein two radicals R$^c$ may together form a divalent bridging group selected from in each case unsubstituted or substituted C₂-C₁₀-alkylene, C₃-C₆-cycloalkylene and C₆-C₁₄-arylene, wherein C₂-C₁₀-alkylene, C₃-C₆-cycloalkylene and C₆-C₁₄-arylene may carry one or more identical or different C₁-C₁₂-alkyl radicals, R$^a$ and R$^b$ are independently of one another selected from the group consisting of hydrogen and unsubstituted C₁-C₆-alkyl, R¹, R², R³, R⁴, R⁵, R⁶, R¹³, R¹⁴, R¹⁵, R¹⁶, R¹⁷, R¹⁸, R⁷, R⁸, R⁹, R¹⁰, R¹¹ and R¹² are independently of one another selected from the group consisting of hydrogen, and in each case unsubstituted or substituted alkyl, alkoxy, alkenyl, alkadienyl, alkynyl, cycloalkyl, cycloalkoxy, bicycloalkyl, cycloalkenyl, heterocycloalkyl, heterocycloalkyloxy, aryl, aryloxy, heteroaryl and heteroaryloxy;

and wherein said compound of the general formula (I) has a linear structure, comprising reacting a compound of the formula (A):

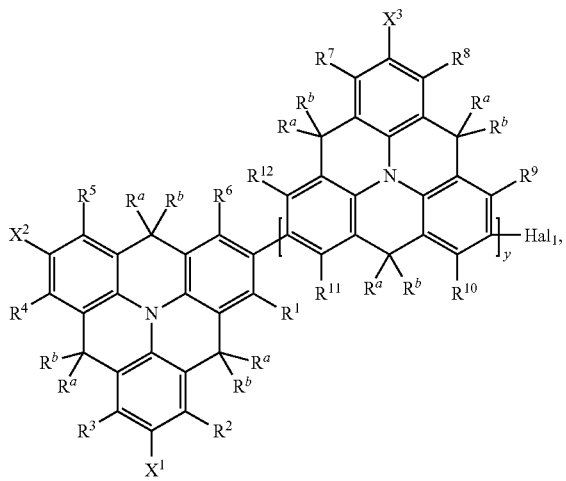

wherein y is 1 to (n-z) and Hal₁ is Cl, Br or I with a compound of the formula (B):

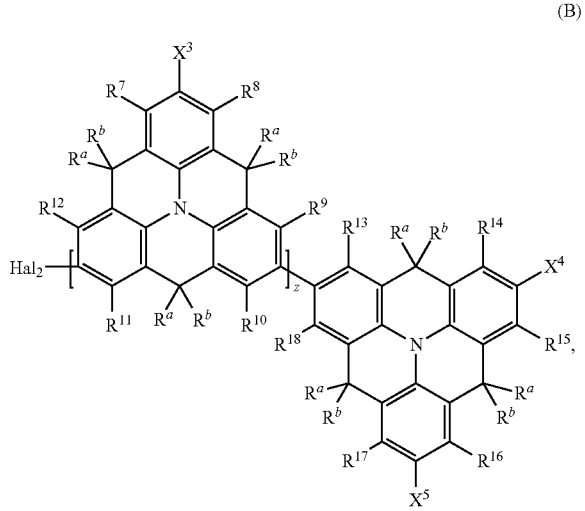

wherein z is 0 to (n-y) and $Hal_2$ is Cl, Br or I,
in the presence of a transition metal-containing catalyst,
with the proviso that the sum of y+z is n.

15. A process according to claim 14, wherein the transition metal-containing catalyst comprises bis(1,5-cyclooctadiene)nickel(0).

16. A dye-sensitized or Perovskite-based photoelectric conversion device comprising at least one compound of the formula (I) as defined in claim 1.

17. A dye-sensitized photoelectric conversion device according to claim 16, comprising:
an electrically conductive layer being part of or forming the working electrode (anode),
a photosensitive layer comprising a semi-conductive metal oxide and a chromophoric substance,
a charge transfer layer comprising at least one compound of the formula (1),
an electrically conductive layer being part of or forming the counter electrode (cathode).

18. A Perovskite-based photoelectric conversion device according to claim 16, comprising:
an electrically conductive layer being part of or forming the working electrode (anode),
a photosensitive layer comprising a Perovskite absorber material,
a charge transfer layer comprising at least one compound of the formula (I),
an electrically conductive layer being part of or forming the counter electrode (cathode).

19. A Perovskite-based photoelectric conversion device according to claim 18, wherein the Perovskite absorber material is selected from compounds of the formula $(R^dNH_3)PbX^a$, wherein $R^d$ is $C_1$-$C_4$ alkyl and $X^a$ is Cl, Br or I.

20. A solar cell which comprises the photoelectric conversion device according to claim 16.

21. An organic field-effect transistor, comprising a substrate having at least one gate structure, a source electrode and a drain electrode and at least one compound of the formula (I) as defined in claim 1 as a semiconductor material.

22. A substrate comprising a plurality of organic field-effect transistors, at least some of the field-effect transistors comprising at least one compound of the formula (I) as defined in claim 1.

23. An electroluminescent arrangement comprising an upper electrode, a lower electrode, wherein at least one of said electrodes is transparent, an electroluminescent layer and optionally an auxiliary layer, wherein the electroluminescent arrangement comprises at least one compound of the formula (I) as defined in claim 1.

24. An electroluminescent arrangement as claimed in claim 23 in form of an organic light-emitting diode (OLED).

25. A bulk heterojunction organic solar cell, comprising at least one compound of the formula (I) as defined in claim 1.

26. A method of making a dye-sensitized- or a Perovskite-based photoelectric conversion device comprising incorporating in the device a compound of general formula (I) as defined in claim 1 as a hole transporting material.

27. The method according to claim 26, wherein said device is an organic field-effect transistor, a bulk heterojunction organic solar cell, or other organic solar cell.

* * * * *